US006554983B2

(12) United States Patent
Imamura et al.

(10) Patent No.: US 6,554,983 B2
(45) Date of Patent: Apr. 29, 2003

(54) GAS SENSING ELEMENT EMPLOYABLE IN AN EXHAUST SYSTEM OF AN INTERNAL COMBUSTION ENGINE

(75) Inventors: Hiroo Imamura, Aichi-ken (JP); Toshitaka Saito, Toyohashi (JP); Keigo Mizutani, Okazaki (JP); Daisuke Makino, Ichinomiya (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/810,180

(22) Filed: Mar. 19, 2001

(65) Prior Publication Data

US 2002/0000376 A1 Jan. 3, 2002

(30) Foreign Application Priority Data

Mar. 17, 2000 (JP) ........................................ 2000-075907

(51) Int. Cl.[7] ............................................. G01N 27/407
(52) U.S. Cl. ...................... 204/425; 204/426; 204/427
(58) Field of Search .................................. 204/421–429

(56) References Cited

U.S. PATENT DOCUMENTS

| 5,672,811 A | | 9/1997 | Kato et al. |
| 6,036,841 A | | 3/2000 | Kato et al. |
| 6,045,673 A | * | 4/2000 | Kato et al. |
| 6,059,947 A | | 5/2000 | Kato et al. |
| 6,068,747 A | * | 5/2000 | Tojo et al. |
| 6,290,829 B1 | * | 9/2001 | Kato et al. |
| 6,383,354 B1 | * | 5/2002 | Kurokawa et al. |

FOREIGN PATENT DOCUMENTS

| JP | 8-271476 | 10/1996 |
| JP | 10-38845 | 2/1998 |
| JP | 11-37972 | 2/1999 |

OTHER PUBLICATIONS

"Performance of Thick Film NOx Sensor on Diesel and Gasoline Engines" by Kato et al., NGK Insulators Ltd., 1997 month unavailable Society of Automotive Engineers, Inc.; pp. 199–206.

* cited by examiner

*Primary Examiner*—T. Tung
(74) *Attorney, Agent, or Firm*—Nixon & Vanderhye P.C.

(57) ABSTRACT

An objective gas is successively introduced into first and second chambers which are connected via a narrow passage. A first monitor cell, provided on a surface of the first chamber, generates an electromotive force representing an oxygen concentration in the first chamber. A second monitor cell, provided on a surface of the second chamber, generates an electromotive force representing an oxygen concentration in the second chamber. A voltage applied to a pump cell is controlled based on the electromotive forces obtained from the first and second monitor cells.

6 Claims, 23 Drawing Sheets

PRIOR ART 1

GAS SENSING ELEMENT EMPLOYABLE IN AN EXHAUST SYSTEM OF AN INTERNAL COMBUSTION ENGINE

BACKGROUND OF THE INVENTION

The present invention relates to a gas sensing element capable of detecting emission gas such as NOx and preferably employable in an exhaust system for an internal combustion engine of an automotive vehicle.

Harmful gases emitted from automotive internal combustion engines cause air pollution as a serious problem the modern society now faces. Various laws and regulations require automotive manufacturers to satisfy severe standards for promoting emission gas purification. Under such circumferences, it is known that the emission gas purification can be effectively performed by directly detecting the NOx concentration to feedback control the engine combustion as well as to monitor the catalyst condition based on the detected NOx value.

FIGS. 9 and 10 show conventional gas sensing elements.

A pump cell 3 faces a first chamber 11. To perform pumping of oxygen between the first chamber 11 and the outside of the sensing element, a voltage is applied to the pump cell 3. A monitor cell 95 detects a concentration of oxygen in the first chamber 11. The pump cell 3 is feedback controlled based on a detected value of monitor cell 95 to maintain a constant oxygen concentration.

A sensor cell 2 faces a second chamber 12. The sensor cell 2 measures oxygen ions produced from NOx in the second chamber 12 and produces a sensor signal (i.e., oxygen ion current) representing a NOx concentration based on the measured oxygen ions. As the oxygen concentration in the second chamber 12 is constant, an amount of oxygen ions moving across the sensor cell 2 is proportional to the NOx concentration. In other words, the oxygen ion current of the sensor cell 2 is proportional to the NOx concentration.

Thus, the NOx concentration can be accurately measured irrespective of change of the oxygen concentration in the measured exhaust gas.

In this case, the sensor cell 2 is made of a material capably of decomposing NOx into oxygen ions and nitrogen ions to measure the NOx concentration. However, when the sensor cell 2 is made of other material, the sensor cell 2 will be able to measure another gas concentration.

However, the conventional gas sensing elements have the following problems.

The monitor cell, provided in the first chamber, cannot accurately monitor the oxygen concentration in the vicinity of the sensor cell provided in the second chamber. A significant difference will appear between the oxygen concentration of the first chamber and that of the second chamber.

The second chamber communicates with the first chamber via a narrow passage (i.e., diffusion resistive passage). Presence of such a narrow passage possibly delays transmission of oxygen concentration change to the second chamber compared with transmission to the first chamber. Accordingly, when the monitor cell is provided in the second chamber, the control of the first chamber is delayed. The response of control is worsened.

SUMMARY OF THE INVENTION

To solve the above-described problems, an object of the present invention is to provide a gas sensing element having excellent response and capable of accurately detecting a specific gas concentration in a measured gas irrespective of unpredictable or unstable distribution of oxygen gas concentration.

In order to accomplish the above and other related objects, the present invention provides a first gas sensing element comprising first and second chambers into which an objective gas to be measured is introduced. A first diffusion resistive passage connects the first chamber to an outside of the gas sensing element. A second diffusion resistive passage connects the first chamber to the second chamber. A pump cell, provided on a surface defining the first chamber, performs pumping of oxygen in accordance with an applied voltage. A first monitor cell, provided on a surface defining the first chamber, generates an electromotive force representing an oxygen concentration in the first chamber. A second monitor cell, provided on a surface defining the second chamber, generates an electromotive force representing an oxygen concentration in the second chamber. A sensor cell, provided on a surface defining the second chamber, is responsive to application of a predetermined voltage for generating a sensor current representing a specific gas concentration in the objective gas. And, the voltage applied to the pump cell is controlled based on the electromotive forces obtained from the first and second monitor cells.

According to the first gas sensing element, the first and second monitor cells face the first and second chambers respectively. The voltage applied to the pump cell is controlled based on the electromotive forces obtained from the first and second monitor cells.

The first gas sensing element of the present invention operates in the following manner.

The first monitor cell interposes between the first chamber and the reference gas chamber. The second monitor cell interposes between the second chamber and the reference gas chamber. Each of the first and second monitor cells generates an electromotive force in response to a measured oxygen concentration.

When the oxygen concentration in the measured gas is stable, there is no substantial difference between the oxygen concentration in the first chamber and the oxygen concentration in the second chamber. Thus, the electromotive force of the first monitor cell is substantially identical with that of the second monitor cell.

In this case, the voltage applied to the pump cell is controlled based on the electromotive force of the second monitor cell because the second monitor cell can accurately monitor the oxygen concentration in the vicinity of the sensor cell due to their positional relationship.

When the oxygen concentration in the measured gas is varying widely, the change of oxygen concentration is transmitted first to the first chamber and then transmitted with a larger delay to the second chamber. In other words, the electromotive force of the first monitor cell is apparently different from that of the second monitor cell.

When the oxygen concentration in the measured gas is increasing gradually, the electromotive force of the first monitor cell becomes smaller than that of the second monitor cell. On the other hand, when the oxygen concentration in the measured gas is decreasing gradually, the electromotive force of the first monitor cell becomes larger than that of the second monitor cell. This is due to time delay required when the measured gas passes through the diffusion resistive passage connecting the first chamber to the second chamber.

In such a transient state, to suppress adverse influence caused by deterioration in response, the voltage applied to the pump cell is controlled based on the electromotive force of the first monitor cell because the first monitor cell can promptly monitor the change of oxygen concentration caused in the measured gas.

As described above, the present invention provides the first gas sensing element which has excellent response and is capable of accurately detecting a specific gas concentration in a measured gas irrespective of unpredictable or unstable distribution of oxygen gas concentration.

Each of the sensor cell, the pump cell, and the monitor cell consists of a pair of electrodes with each electrode being made of a material individually selected considering the position where the cell is provided.

For example, the sensor cell has an electrode facing the second chamber. This electrode is required to have a function of generating oxygen ions from the specific gas to be detected.

The pump cell and the monitor cell have electrodes facing the first and second chambers. Preferably, these electrodes are inactive against the specific gas to be detected.

With this arrangement, it becomes possible to cause the decomposition of the specific gas in a limited region on the sensor cell, thereby enabling accurate measurement of specific gas concentration.

According to the first gas sensing element of the present invention, it is preferable that the first monitor cell and the second monitor cell are connected in parallel with each other.

This provides a simplified circuit arrangement for obtaining an average of the electromotive forces produced from the first and second monitor cells.

The present invention provides a second gas sensing element comprising first and second chambers into which an objective gas to be measured is introduced. A first diffusion resistive passage connects the first chamber to an outside of the gas sensing element. A second diffusion resistive passage connects the first chamber to the second chamber. A pump cell, provided on a surface defining the first chamber, performs pumping of oxygen in accordance with an applied voltage. A monitor cell is provided on either a surface defining the first chamber or a surface defining the second chamber. A sensor cell, provided on a surface defining the second chamber and responsive to application of a predetermined voltage, generates a sensor current representing a specific gas concentration in the objective gas. And, the voltage applied to the pump cell is controlled based on a limiting current obtained when a voltage is applied to the monitor cell.

The monitor cell is arranged to function as an oxygen concentration sensor in response to application of a voltage. The monitor cell produces an output current whose magnitude basically changes in accordance with an applied voltage but does not change in a specific voltage range irrespective of change of the applied voltage. The constant output current corresponding to the specific voltage range is generally referred to as a limiting current.

When the monitor cell faces the first chamber, the oxygen concentration in the first chamber is known from the limiting current value of the monitor cell. Thus, the oxygen concentration in the second chamber can be set to a lower constant value by controlling the voltage applied to the pump cell based on the limiting current value of the monitor cell. Furthermore, two-stage pumping is performed at the upstream of the sensor cell. Namely, pumping at the monitor cell and pumping at the pump cell are performed in the first chamber. This makes it possible to suppress the oxygen concentration dependency in the specific gas concentration detection.

Furthermore, as a voltage is applied to the monitor cell, the monitor cell is capable of pumping oxygen in the first chamber.

Therefore, when the oxygen concentration in the measured gas changes widely in a certain time period, variation of the oxygen concentration is followed up by the pumping function of the monitor cell. No problem will be caused due to delay in response.

When the monitor cell faces the second chamber, the oxygen concentration in the second chamber is known from the limiting current value of the monitor cell. Thus, the oxygen concentration in the second chamber can be set to a lower constant value by controlling the voltage applied to the pump cell based on the limiting current value of the monitor cell.

As the pump cell is controlled based on the oxygen concentration in the vicinity of the sensor cell, it becomes possible to accurately detect the specific gas concentration when the oxygen gas concentration is stable in a certain time period and there is a spatial distribution of oxygen concentration (i.e., when the oxygen concentration in the first chamber is different from that in the second chamber).

Furthermore, as a voltage is applied to the monitor cell, the monitor cell is capable of pumping oxygen in the second chamber.

Therefore, when the oxygen concentration in the measured gas changes widely in a certain time period, variation of oxygen concentration is followed up by the pumping function of monitor cell. No problem will be caused due to delay in response.

Accordingly, the second gas sensing element of the present invention makes it possible to accurately detect the specific gas concentration irrespective of change of oxygen gas concentration in the measured gas. Furthermore, according to the second gas sensing element of the present invention, the measured current of the monitor cell is utilized to control the pump cell.

This is effective to reduce error caused by offset current obtained when the specific gas concentration is 0, thereby realizing highly accurate detection of the specific gas concentration. The offset current is generally caused due to residual oxygen or leak current of each cell.

As described above, the present invention provides the second gas sensing element which has excellent response and is capable of accurately detecting a specific gas concentration in a measured gas irrespective of unpredictable or unstable distribution of oxygen gas concentration.

If an excessively high voltage is applied to the pump cell, there is the possibility that the specific gas may decompose even in a case where the electrode of the pump cell is a material inactive to the specific gas.

In view of the above, it is preferable to measure a current value of the pump cell and measure the oxygen concentration of the measured gas, and adjust the limiting current value in accordance with the measured value.

The present invention provides a third gas sensing element comprising first and second chambers into which an objective gas to be measured is introduced. A first diffusion resistive passage connects the first chamber to an outside of the gas sensing element. A second diffusion resistive passage connects the first chamber to the second chamber. A first pump cell, provided on a surface defining the first chamber, performs pumping of oxygen in accordance with an applied voltage. A second pump cell, provided on a surface defining the second chamber, performs pumping of oxygen in accordance with an applied voltage. A sensor cell, provided on a surface defining the second chamber and responsive to application of a predetermined voltage, generates a sensor current representing a specific gas concentration in the objective gas. A pump current is produced from at least one of the first and second pump cells in accordance with the pumping of oxygen. And, the pump current is utilized to control the voltage applied to the one of the first and second pump cells.

As described later with reference to FIG. 18, the pump cell current does not change in a predetermined voltage range of the applied voltage. This constant current value, i.e., the limiting current value, is dependent on the oxygen concentration.

Accordingly, the oxygen concentration in each chamber can be maintained at a constant value by adjusting the voltage applied to the pump cell in accordance with the pump current.

Furthermore, the third gas sensing element of the present invention comprises two pump cells which individually perform pumping in respective chambers. Thus, undesirable distribution of oxygen concentration will not appear in each chamber.

Moreover, even in a transient state where the oxygen concentration is widely changing, the response will not be so delayed because the pumping is independently performed in each chamber.

As described above, the present invention provides the third gas sensing element which has excellent response and is capable of accurately detecting a specific gas concentration in a measured gas irrespective of unpredictable or unstable distribution of oxygen gas concentration.

Furthermore, the third gas sensing element of the present invention does not require a monitor cell. Thus, the arrangement and control mechanism of the gas sensor can be simplified. Meanwhile, it is possible to provide a monitor cell as shown in a later-described fourth embodiment.

The present invention provides a fourth gas sensing element comprising first and second chambers into which an objective gas to be measured is introduced. A first diffusion resistive passage connects the first chamber to an outside of the gas sensing element. A second diffusion resistive passage connects the first chamber to the second chamber. A monitor cell is provided on at least one of a surface defining the first chamber or a surface defining the second chamber. A first pump cell, provided on a surface defining the first chamber, performs pumping of oxygen in accordance with an applied voltage. A second pump cell, provided on a surface defining the second chamber, performs pumping of oxygen in accordance with an applied voltage. A sensor cell, provided on a surface defining the second chamber and responsive to application of a predetermined voltage, generates a sensor current representing a specific gas concentration in the objective gas. And, the voltage applied to at least one of the first and second pump cells is controlled based on a limiting current obtained when a voltage is applied to the monitor cell.

According to the fourth gas sensing element of the present invention, the voltage applied to the pump cell can be controlled based on the limiting current obtained when a voltage is applied to the monitor cell. Thus, like the second gas sensing element, it becomes possible to reduce error caused by offset current obtained when the specific gas concentration is 0, thereby realizing highly accurate detection of the specific gas concentration.

Furthermore, the fourth gas sensing element of the present invention is based on a two-stage control of oxygen concentration using the first and second pump cells. Thus, like the third gas sensing element, the response will not be so delayed because the pumping is independently performed in each chamber.

As described above, the present invention provides the fourth gas sensing element which has excellent response and is capable of accurately detecting a specific gas concentration in a measured gas irrespective of unpredictable or unstable distribution of oxygen gas concentration.

According to the first to fourth gas sensing elements, it is preferable that each pump cell is provided on a surface defining a reference gas chamber.

This arrangement is preferably employed when the gas sensing element of the present invention detects a specific gas component involved in the exhaust gas of an internal combustion engine. More specifically, when the air-fuel ratio is shifted to a rich side, the measurement of the specific gas concentration is easily performed.

The gas sensing element of the present invention is applicable not only to a NOx sensor but also applicable to other types of gas sensors, such as a CO sensor, a CO2 sensor, a H2O sensor, a SOx sensor.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Figure 1:
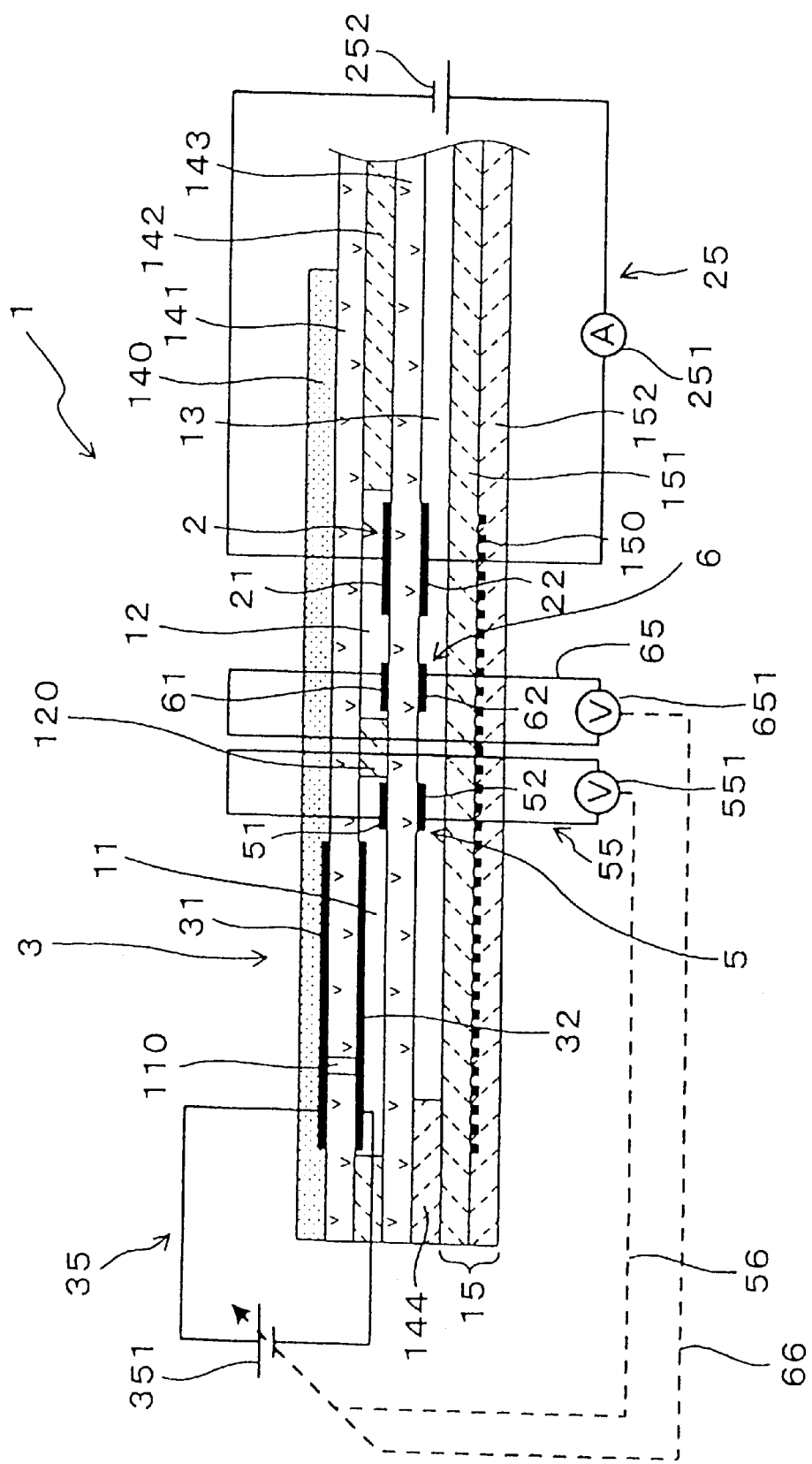
FIG. 1 is a cross-sectional view showing a gas sensing element in accordance with a first embodiment of the present invention.

Preferred embodiments of the present invention will be explained hereinafter with reference to attached drawings. Identical parts are denoted by the same reference numerals throughout the drawings.

First Embodiment

A gas sensing element of a first embodiment will be explained with reference to FIGS. 1 to 10.

Figure 2:
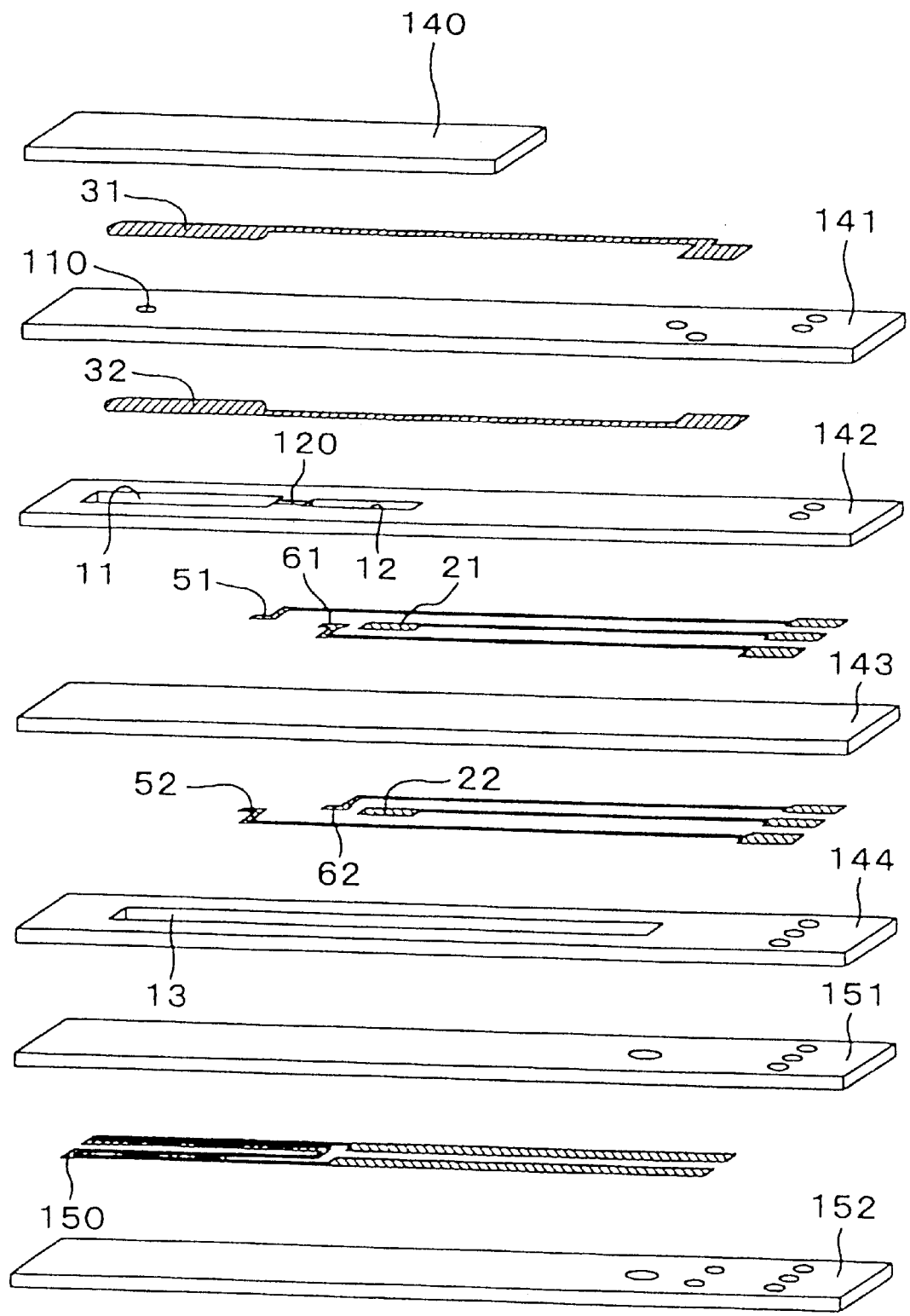
FIG. 2 is a perspective exploded view showing the gas sensing element in accordance with the first embodiment of the present invention.

As shown in FIGS. 1 and 2, a gas sensing element 1 of the first embodiment comprises two chamber, i.e., a first chamber 11 and a second chamber 12, into which an objective gas to be measured is introduced. A first diffusion resistive passage 110 connects the first chamber 11 to an outside of the gas sensing element 1. A second diffusion resistive passage 120 connects the first chamber 11 to the second chamber 12. A pump cell 3, located or provided on a surface defining the first chamber 11, performs pumping of oxygen in accordance with an applied voltage.

A first monitor cell 5, located or provided on a surface defining the first chamber 11, generates an electromotive force representing an oxygen concentration in the first chamber 11. A second monitor cell 6, located or provided on a surface defining the second chamber 12, generates an electromotive force representing an oxygen concentration in the second chamber 12. A sensor cell 2, located or provided on a surface defining the second chamber 12, is responsive to application of a predetermined voltage for generating a sensor current representing a specific gas concentration in the objective gas. And, the voltage applied to the pump cell 3 is controlled based on the electromotive forces obtained from the first monitor cell 5 and the second monitor cell 6.

The gas sensing element 1 is incorporated in a gas sensor 7 as later-described and installed in an exhaust pipe of an automotive engine to measure NOx concentration in the exhaust gas for the purposes of controlling engine combustion and monitoring an exhaust gas purification catalyst.

The arrangement of the gas sensing element 1 of the first embodiment will be explained in more detail.

As shown in FIG. 1, the gas sensing element 1 of the first embodiment comprises a first solid electrolytic sheet 141, a first spacer 142, a second solid electrolytic sheet 143, a second spacer 144, and a heater 15 which are successively stacked in this order so as to constitute a multilayered sensor structure. The first spacer 142, interposed between the first solid electrolytic sheet 141 and the second solid electrolytic sheet 143, defines the first chamber 11 and the second chamber 12. The second spacer 144 defines a reference gas chamber 13. Upon supply of electric power, the heater 15 generates heat to warm the sensor cell 2, monitor cell 5 and pump cell 6 up to their activation temperatures.

The sensor cell 2 consists of a pair of sensor electrodes 21 and 22 located or provided on upper and lower surfaces of the second solid electrolytic sheet 143. The sensor electrodes 21 and 22 are connected to a power source 252 and an ammeter 251 to constitute a sensor circuit 25.

One sensor electrode 21 is located or provided on a surface defining the second chamber 12, while the other sensor electrode 22 is located or provided on a surface defining the reference gas chamber 13.

The reference gas chamber 13 is filled with air serving as the reference gas.

The pump cell 3 consists of a pair of pump electrodes 31 and 32 located or provided on upper and lower surfaces of the first solid electrolytic sheet 141. The pump electrodes 31 and 22 are connected to a power source 351 to constitute a pump circuit 35.

One pump electrode 31 is located or provided at an outermost side but a porous protecting layer 140. Thus, the pump electrode 31 faces the outside of the gas sensing element 1. The other pump electrode 32 is located or provided on a surface defining the first chamber 11. The first diffusion resistive passage 110 extends vertically so as to penetrate all of these pump electrodes 31 and 32 as well as the first solid electrolytic sheet 141 (although not clearly shown in the drawing). The first diffusion resistive passage 110 and the second diffusion resistive passage 120 are pin holes but can be constituted by porous layers.

The first monitor cell 5 consists of a pair of monitor electrodes 51 and 52 located or provided on upper and lower surfaces of the second solid electrolytic sheet 143. The monitor electrodes 51 and 52 are connected to a first voltmeter 551 to constitute a first monitor circuit 55.

Similarly, the second monitor cell 6 consists of a pair of monitor electrodes 61 and 62 located or provided on upper and lower surfaces of the second solid electrolytic sheet 143.

The monitor electrodes 61 and 62 are connected to a second voltmeter 651 to constitute a second monitor circuit 65.

An output signal of the first monitor circuit 55 is sent to the pump circuit 35 via a feedback circuit 56. An output signal of the second monitor circuit 65 is sent to the pump circuit 35 via a feedback circuit 66.

One monitor electrode 51 is located or provided on a surface defining the first chamber 11. Another monitor electrode 61 is located or provided on a surface defining the second chamber 12. The other monitor electrodes 52 and 62 are located or provided on a surface defining the reference gas chamber 13.

Both of the first solid electrolytic sheet 141 and the second solid electrolytic sheet 143 are zirconia members having oxygen ion conductivity. The pump electrode 31, sensor electrode 22, and monitor electrodes 52 and 62 are Pt or comparable noble metal. The pump electrode 32 and the monitor electrodes 51 and 61 are Pt—Au or comparable noble metal which is inactive against NOx. The sensor electrode 21 is Pt—Ph or comparable noble metal which is active against NOx. In this case, active/inactive represents capability/incapability of decomposing NOx into oxygen ions and nitrogen ion.

Each of the spacers 142 and 144 are an insulating alumina member. The porous protecting layer 140 is an insulating ceramic member.

The heater 15 comprises a pair of insulating substrates 151 and 152 and a heating element 150 interposed between these heater substrates 151 and 152. The heating element 150 generates heat upon receiving electric power. The heater substrates 151 and 152 are alumina members. The heating element 150 is a platinum member.

Figure 3:
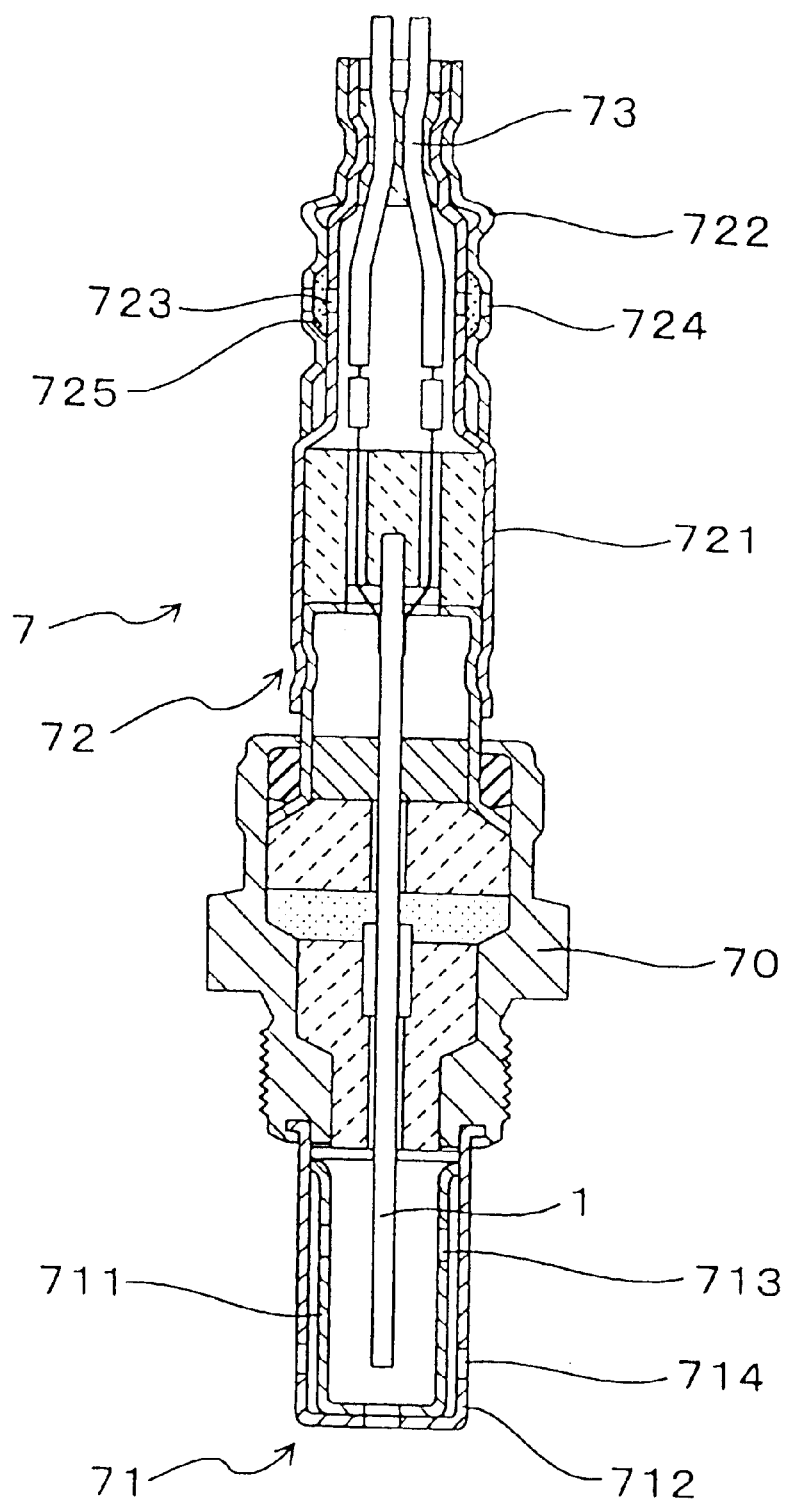
FIG. 3 is a vertical cross-sectional view showing a gas sensor incorporating the gas sensing element in accordance with the first embodiment of the present invention.

FIG. 3 shows a gas sensor 7 incorporating the sensing element 1 of the present invention. The gas sensor 7 comprises a cylindrical housing 70 accommodating the gas sensing element 1 surrounded by an insulating material.

The front end (i.e., distal end) of the gas sensing element 1 protrudes in the axial frontward direction (i.e., downward direction) from the housing 70 and is surrounded and accommodated in an exhaust cover 71. The exhaust cover 71 is a cup-shaped member fixed to the front end of the housing 70.

The exhaust cover 71 comprises an inner cover 711 and an outer cover 712 which are coaxially disposed stainless members cooperatively constituting a double-wall structure. Each of the inner and outer covers 711 and 712 has a cylindrical wall and a bottom on which a plurality of holes 713 and 714 are properly formed to introduce exhaust gas (i.e., objective gas) into the exhaust cover 71.

An atmosphere cover 72, consisting of a cylindrical main cover 721 and a sub cover 722 overlapped with each other, is fixed to the rear end of the housing 70. These main cover 721 and the sub cover 722 have opposing holes 723 and 724 through which air is introduced into the atmosphere cover 72.

A water repellent filter 725 is provided in a closed space between the main cover 721 and the sub cover 722 at the position corresponding to the air introducing holes 723 and 724. The atmosphere cover 72 has a rear end opening through which lead wires 73 extend to the outside. The lead wires 73 are connected to the rear end (i.e., proximal end) of the gas sensing element 1.

The above-described gas sensing element 1 of the first embodiment operates in the following manner.

The exhaust gas enters into the first chamber 11 via the porous protecting layer 140 and the first diffusion resistive passage 110. A total diffusion resistance of the porous protecting layer 140 and the first diffusion resistive passage 110 determines an exhaust gas amount to be introduced into the first chamber 11.

In the first chamber 11, the pump cell 3 ionizes oxygen contained in the exhaust gas. The pump cell 3 allows the oxygen ion to move between the first chamber 11 and the outside of the gas sensing element 1. This is referred to as pumping of oxygen in the first chamber 11.

The first monitor cell 5, facing the first chamber 11, has the capability of generating an electromotive force representing the oxygen concentration. The first voltmeter 551 of the first monitor circuit 55 measures the electromotive force generated from the first monitor cell 5. Similarly, the second monitor cell 6, facing the second chamber 12, has the capability of generating an electromotive force representing the oxygen concentration. The second voltmeter 651 of the second monitor circuit 65 measures the electromotive force generated from the second monitor cell 6.

A difference between the electromotive forces measured by voltmeters 551 and 651 is sent via feedback circuits 55 and 65 to the pump circuit 35. In the pump circuit 35, the voltage value of power source 351 is controlled to an adequate value based on this feedback signal so as to control the oxygen pumping amount of the pump cell 3.

The oxygen pumping amount is controlled in the following manner.

When the oxygen concentration in the measured gas is stable, there is no substantial difference between the electromotive force produced from the first monitor cell 5 and the electromotive force produced from the second monitor cell 6. In this case, the voltage applied to the pump cell 3 is controlled based on the electromotive force of the second monitor cell 6 because the second monitor cell 6 can accurately monitor the oxygen concentration in the vicinity of the sensor cell 2 as apparent from the positional relationship of the second monitor cell 6 with respect to the sensor cell 2. This is effective to eliminate the error caused due to oxygen concentration distribution in the first and second chambers 11 and 12.

When the oxygen concentration in the measured gas is varying widely, the electromotive force of the first monitor cell 5 is apparently different from that of the second monitor cell 6.

When the oxygen concentration in the measured gas is increasing gradually, the electromotive force of the first monitor cell 5 becomes smaller than that of the second monitor cell 6. On the other hand, when the oxygen concentration in the measured gas is decreasing gradually, the electromotive force of the first monitor cell 5 becomes larger than that of the second monitor cell 6.

This is due to time delay required when the measured gas passes through the second diffusion resistive passage 120 connecting the first chamber 11 to the second chamber 12. Thus, the change of the oxygen concentration in the measured gas is transmitted to the second chamber 12 with a relatively large delay time.

In such a transient state, to suppress adverse influence caused by deterioration in response, the voltage applied to the pump cell 3 is controlled based on the electromotive force of the first monitor cell 5 because the first monitor cell 5 can promptly monitor the change of oxygen concentration caused in the measured gas.

In this control, the voltage applied to the pump cell 3 is controlled in such a manner that detection values of the voltmeters 551 and 651 in the monitor circuits 55 and 65 are within a range of 300 mV to 500 mV. With this arrangement, the oxygen concentration in each of the first chamber 11 and the second chamber 12 can be suppressed to a level of 1 ppm or less which does not give adverse influence to the NOx concentration measurement.

Figure 4:
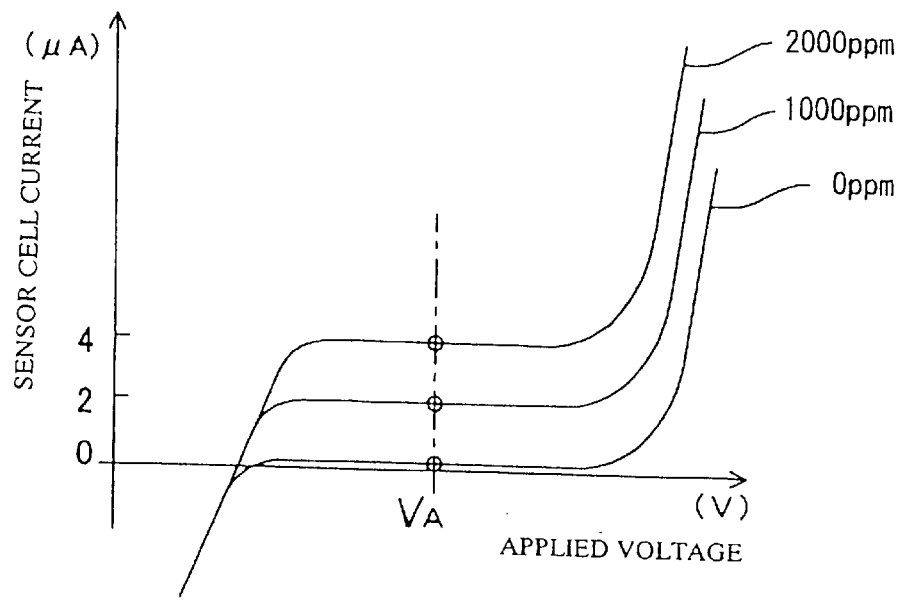
FIG. 4 is a graph showing relationship between NOx concentration and sensor cell current in relation to oxygen concentration in accordance with the first embodiment of the present invention as well as a first conventional example.

FIG. 4 is a graph showing relationship between NOx concentration in the measured gas, sensor cell voltage, and sensor cell current in accordance with the first embodiment of the present invention.

A predetermined voltage $V_A$ is always applied to the sensor cell 2. When the sensor cell current measured in the sensor circuit 25 is 0.2 $\mu A$, 2 $\mu A$ and 3.8 $\mu A$, corresponding NOx concentration is 0 ppm, 1,000 ppm and 2,000 ppm, respectively. In this manner, linearity is maintained between the sensor cell current and the NOx concentration.

Figure 9:
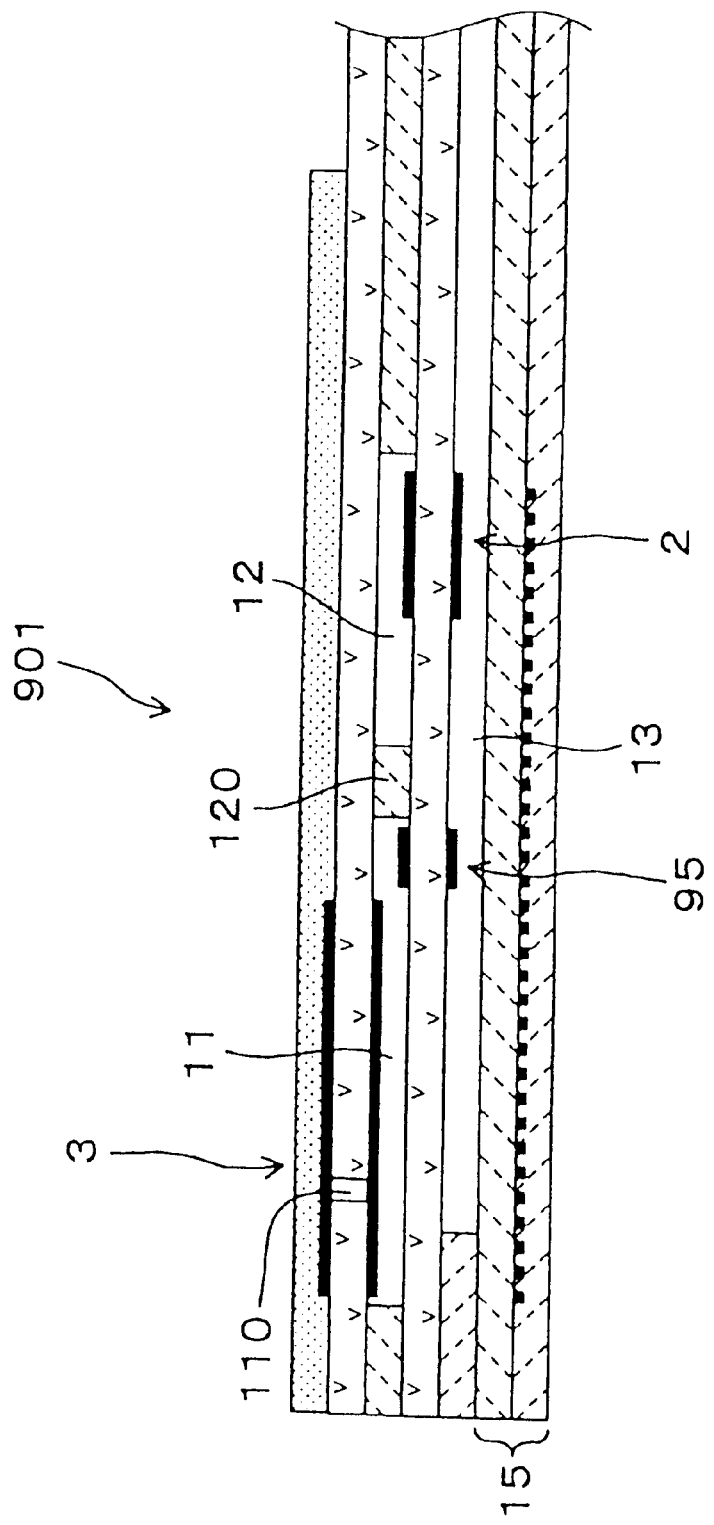
FIG. 9 is a cross-sectional view showing the first conventional example.
Figure 10:
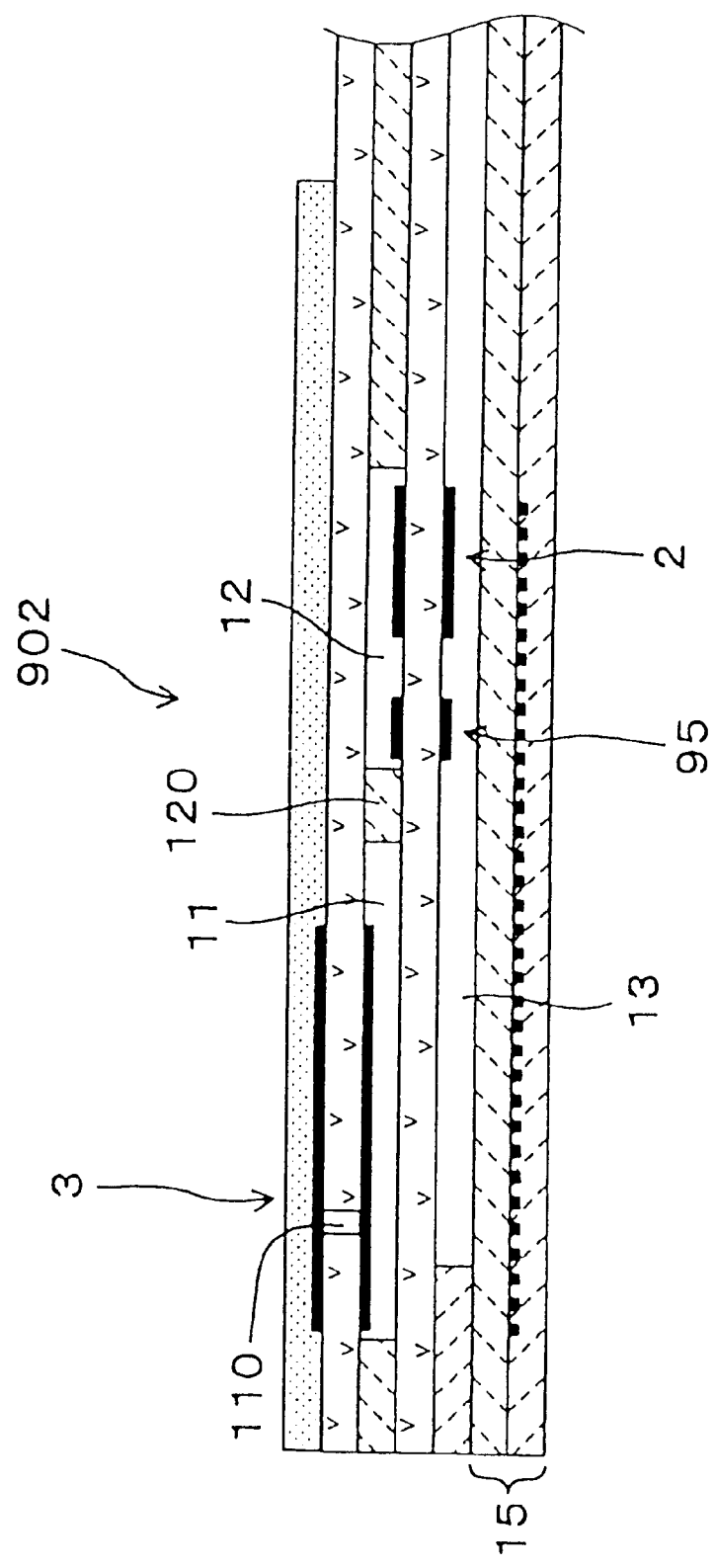
FIG. 10 is a cross-sectional view showing the second conventional example.

Next, the gas sensing element 1 of the first embodiment is evaluated in performance compared with the first and second conventional examples, i.e., gas sensing element 901 and 902 shown in FIGS. 9 and 10.

The gas sensing element 901 (i.e., first conventional example) is characterized in that both the pump cell 3 and a monitor cell 95 face the first chamber 11 while the sensor cell 2 faces the second chamber 12.

The gas sensing element 902 (i.e., second conventional example) is characterized in that the pump cell 3 faces the first chamber 11 while both the monitor cell 95 and the sensor cell 2 face the second chamber 12.

<Performance Evaluation 1: Oxygen Concentration Dependency>

To check oxygen concentration dependency, the gas sensing element 1 of the first embodiment was incorporated in the gas sensor 7 shown in FIG. 3. Then, the gas sensor 7 was exposed to sample gases having different oxygen concentrations to measure NOx concentration. Similarly, each of conventional gas sensing elements 901 and 902 was subjected to the same sample gases to measure NOx concentrations.

The sample gases, prepared for this performance test, were differentiated to have different compositions, e.g., (oxygen 1%, nitrogen 99%), (oxygen 5%, nitrogen 95%), and (oxygen 20%, nitrogen 80%), respectively. In this test, NOx concentration was changed from 0 to 1,000 ppm for each sample gas. The sensor cell current was measured by the ammeter 251 in the sensor circuit 25.

<Performance Evaluation 2: Response>

To check response, the gas sensor 7 incorporating the gas sensing element 1 of the first embodiment was exposed to another sample gas containing 1,000 ppm NOx and 1% oxygen. In this response test, the oxygen concentration was changed from 1% to 20% at a later timing to monitor the change of voltage applied to the pump cell 3. The same test was conducted for each of the conventional gas sensing elements 901 and 902.

Figure 5:
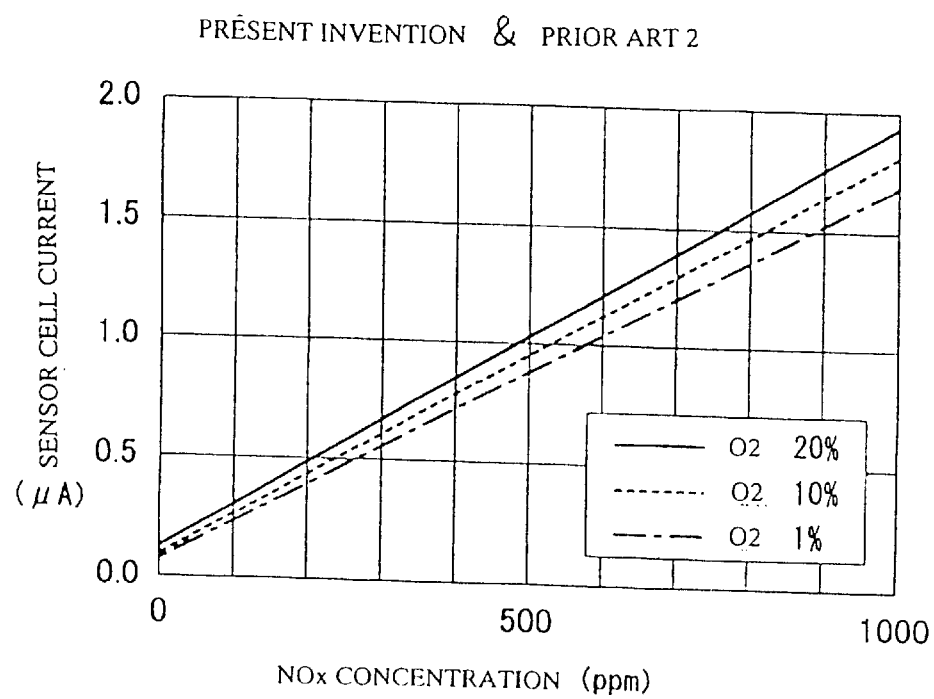
FIG. 5 is a graph showing relationship between NOx concentration and sensor cell current in relation to oxygen concentration according to the first embodiment of the present invention as well as according to a second conventional example.
Figure 7:
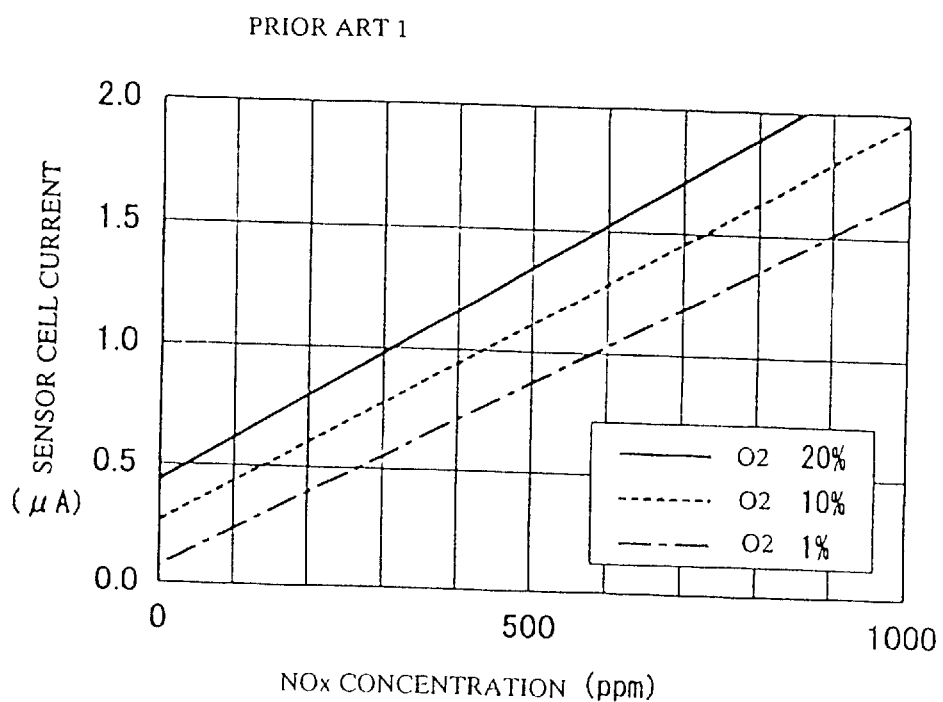
FIG. 7 is a graph showing relationship between NOx concentration and sensor cell current in relation to oxygen concentration according to the first conventional example.

FIGS. 5 and 7 shows the result of performance evaluation 1.

As shown in FIG. 7, according to the first conventional example (i.e., gas sensing element 901), the sensor sell current varies largely in accordance with variation of the oxygen concentration.

Meanwhile, as shown in FIG. 5, according to the gas sensing element 1 of the first embodiment or according to the second conventional example (i.e., gas sensing element 902), the sensor sell current does not vary so largely in accordance with variation of the oxygen concentration.

Figure 6:
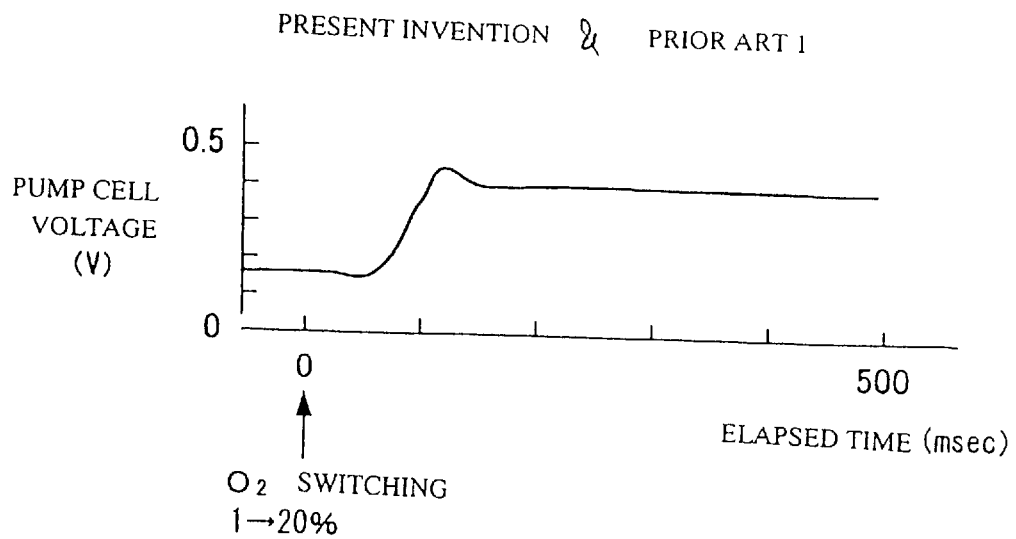
FIG. 6 is a graph showing time variation of pump cell voltage according to the first embodiment of the present invention as well as according to the first conventional example.
Figure 8:
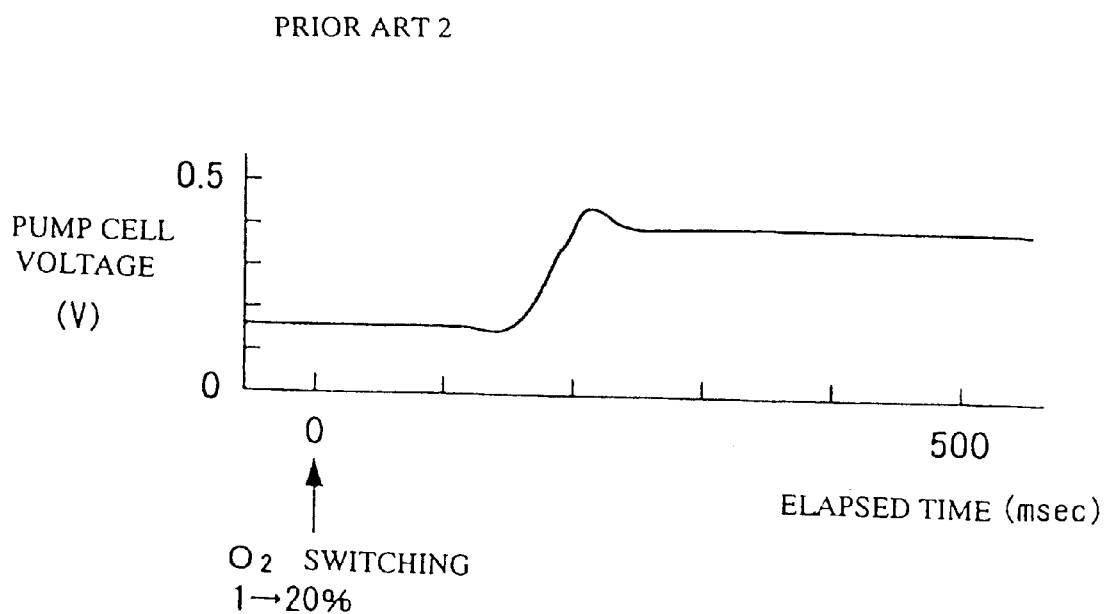
FIG. 8 is a graph showing time variation of pump cell voltage according to the second conventional example.

FIGS. 6 and 8 show the result of performance evaluation 2.

As shown in FIG. 6, according to the gas sensing element 1 of the first embodiment or according to the first conventional example (i.e., gas sensing element 901), the voltage applied to the pump cell 3 has shown change responsive to the switching of oxygen concentration with relatively short delay time of approximately 60 msec. This demonstrates that prompt control has been performed based on the signal of monitor cell 95 or 5. On the other hand, the second conventional example (i.e., gas sensing element 902) required relatively long delay time of approximately 150 msec.

As described above, the gas sensing element 1 of the first embodiment has excellent response and is capable of surely detecting the NOx concentration irrespective of distribution of oxygen concentration. The first conventional example has undesirable oxygen concentration dependency although its response is excellent. The second conventional example has bad response although detection of NOx concentration is accurate.

The gas sensing element of the first embodiment has the first monitor cell 5 facing the first chamber 11 and the second monitor cell 6 facing the second chamber 12. Detection signals of the first monitor cell 5 and the second monitor cell 6 are selectively used for controlling the voltage of the pump cell 3 with reference to stable/unstable state of the oxygen concentration.

Accordingly, the first embodiment provides a NOx sensing element having excellent response and capable of accurately detecting the NOx concentration even when there is certain distribution in the oxygen gas concentration.

As described above, the first embodiment of the present invention provides a gas sensing element which has excellent response and is capable of accurately detecting a specific gas concentration in a measured gas irrespective of unpredictable or unstable distribution of oxygen gas concentration.

Although the first embodiment discloses a Nox gas sensing element, it is however readily understood that the gas sensing element of the first embodiment can be modified into a CO gas sensing element when the electrode of the sensor cell is replaced by a material capable of decomposing CO into carbon ion and oxygen ion. Similarly, the gas sensing element of the first embodiment can be used for detecting other gases, such as CO2, H2O and SOx.

Second Embodiment

Figure 11:
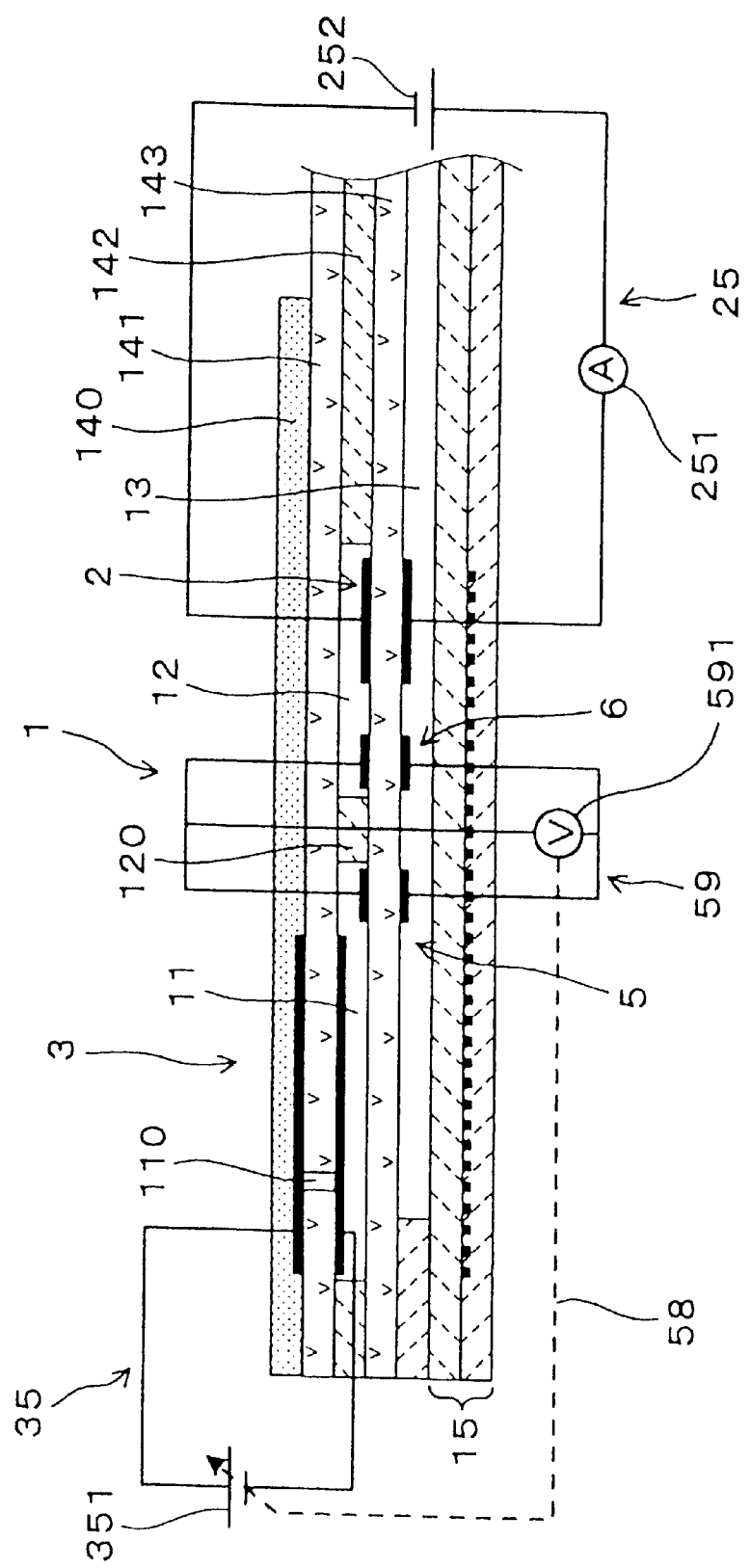
FIG. 11 is a cross-sectional view showing a gas sensing element in accordance with a second embodiment of the present invention.
Figure 12:
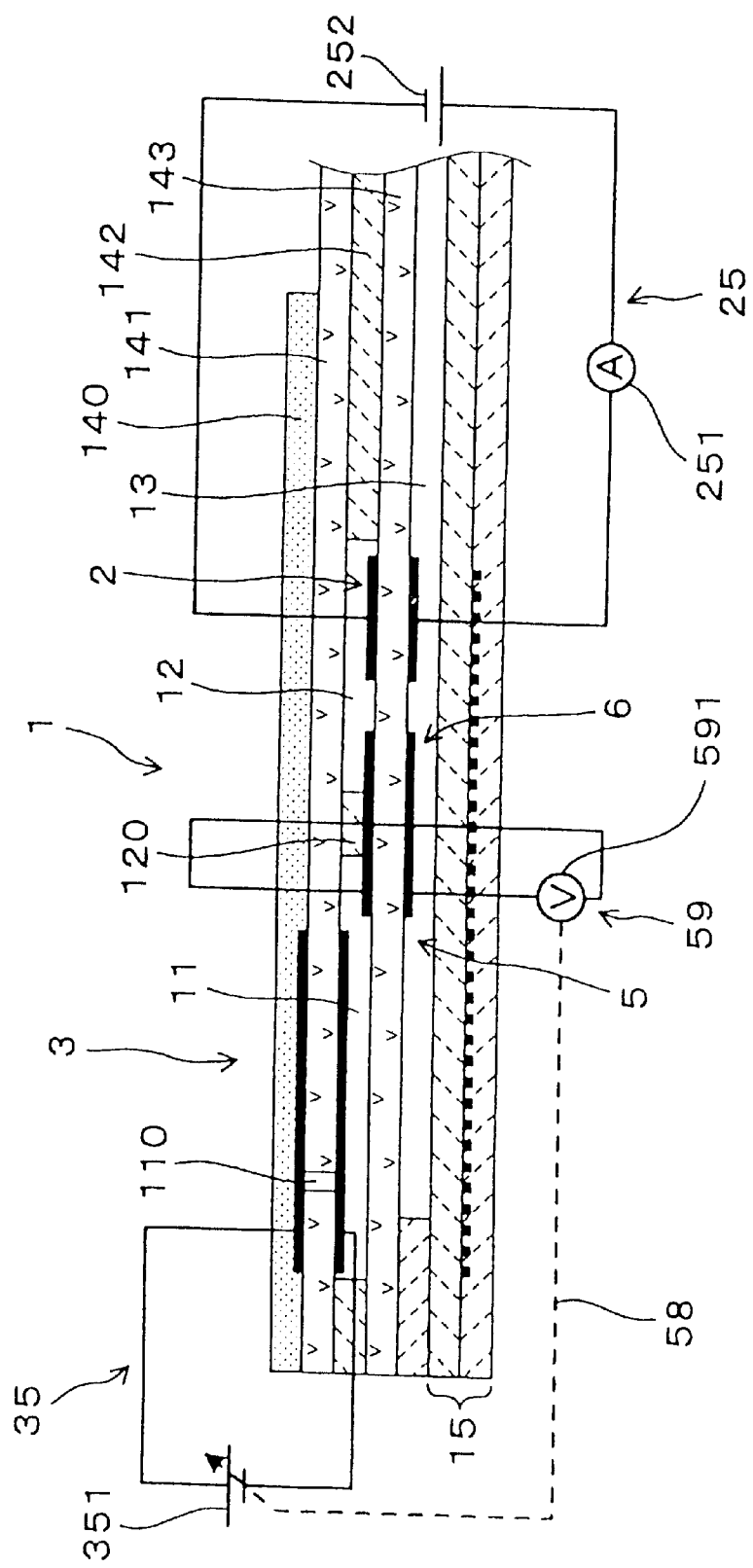
FIG. 12 is a cross-sectional view showing another gas sensing element in accordance with the second embodiment of the present invention.

As shown in FIGS. 11 and 12, a gas sensing element of a second embodiment is characterized in that the first monitor cell and the second monitor cell are connected in parallel with each other.

According to the gas sensing element 1 shown in FIG. 11, each of the first monitor cell 5 and the second monitor cell 6 is connected in parallel with a common monitor circuit 59.

The monitor circuit 59 comprises a voltmeter 591 which measures an average of electromotive forces produced from the monitor cells 5 and 6. A feedback circuit 58 controls the voltage applied to the pump cell 3 based on the measured value of the voltmeter 591. The rest of arrangement is substantially identical with that of the first embodiment.

When the oxygen concentration in the measured gas is stable, there is no substantial difference between the electromotive force produced from the first monitor cell 5 and the electromotive force produced from the second monitor cell 6.

When the oxygen concentration in the measured gas is varying, the measured value of the voltmeter 591 becomes larger or smaller compared with the value obtained in the stable state. Accordingly, the value of voltmeter 591 in the stable state is measured beforehand as a reference value. When there is a difference between the measured value of voltmeter 591 and the reference value, the voltage applied to the pump cell 3 is controlled so as to eliminate this difference.

In this manner, according to the second embodiment, the pump cell 3 can be controlled by using an output value of the voltmeter 591. This makes it possible to simplify the control mechanism.

The second embodiment operates in the same manner as the first embodiment and brings substantially the same effects.

According to the gas sensing element 1 shown in FIG. 12, the first monitor cell 5 and the second monitor cell 6 are integrally formed via the second diffusion resistive passage 120. This arrangement is advantageous in that formation of electrode can be simplified and wiring arrangement for connecting the electrode to the monitor circuit 59 can be simplified. As a result, manufacturing of the gas sensing element can be simplified.

The rest of arrangement is substantially identical with that of the first embodiment, operating in substantially the same manner and bringing substantially the same effects as the first embodiment.

Third Embodiment

Figure 13:
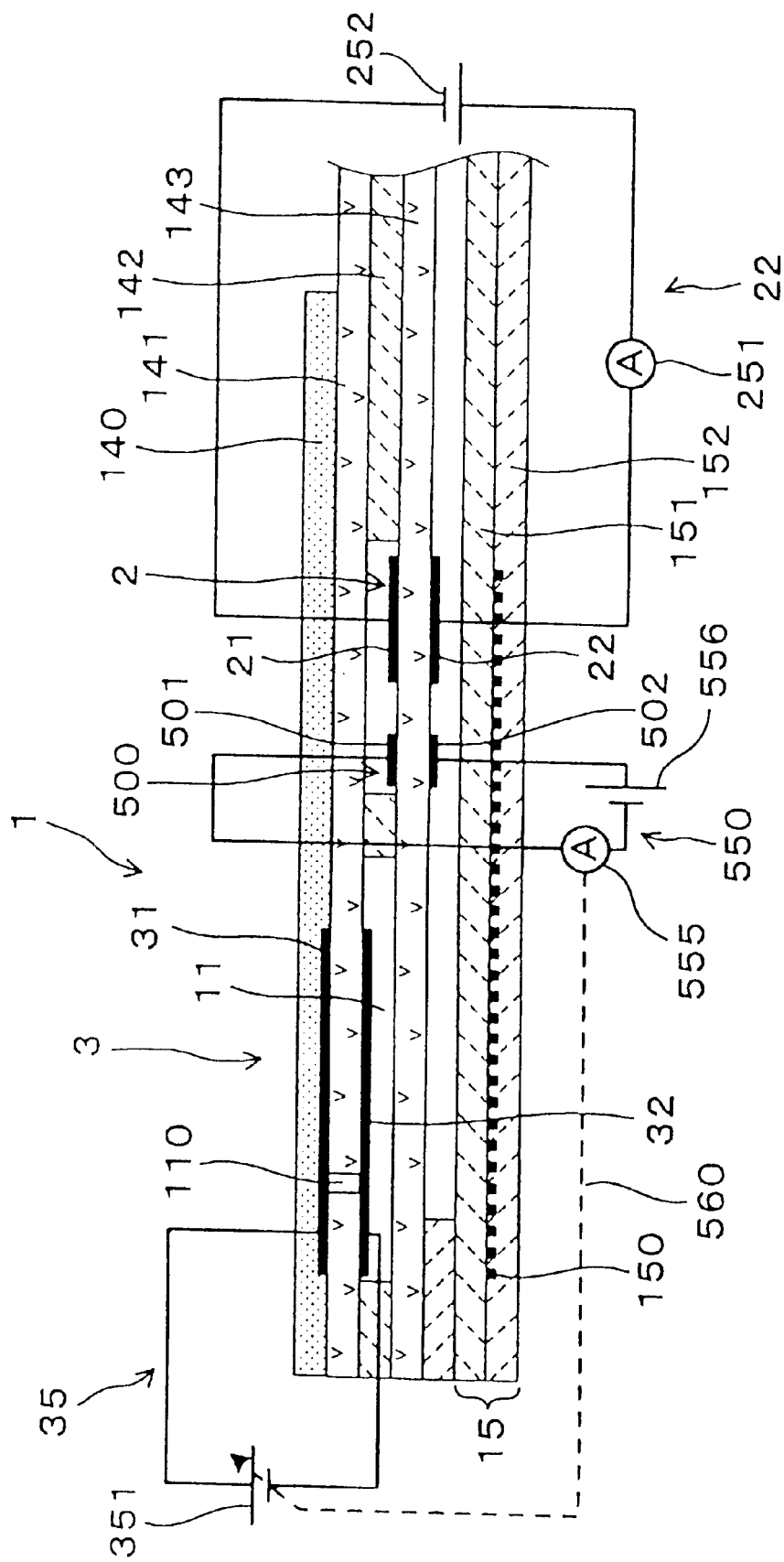
FIG. 13 is a cross-sectional view showing a gas sensing element in accordance with a third embodiment of the present invention.
Figure 14:
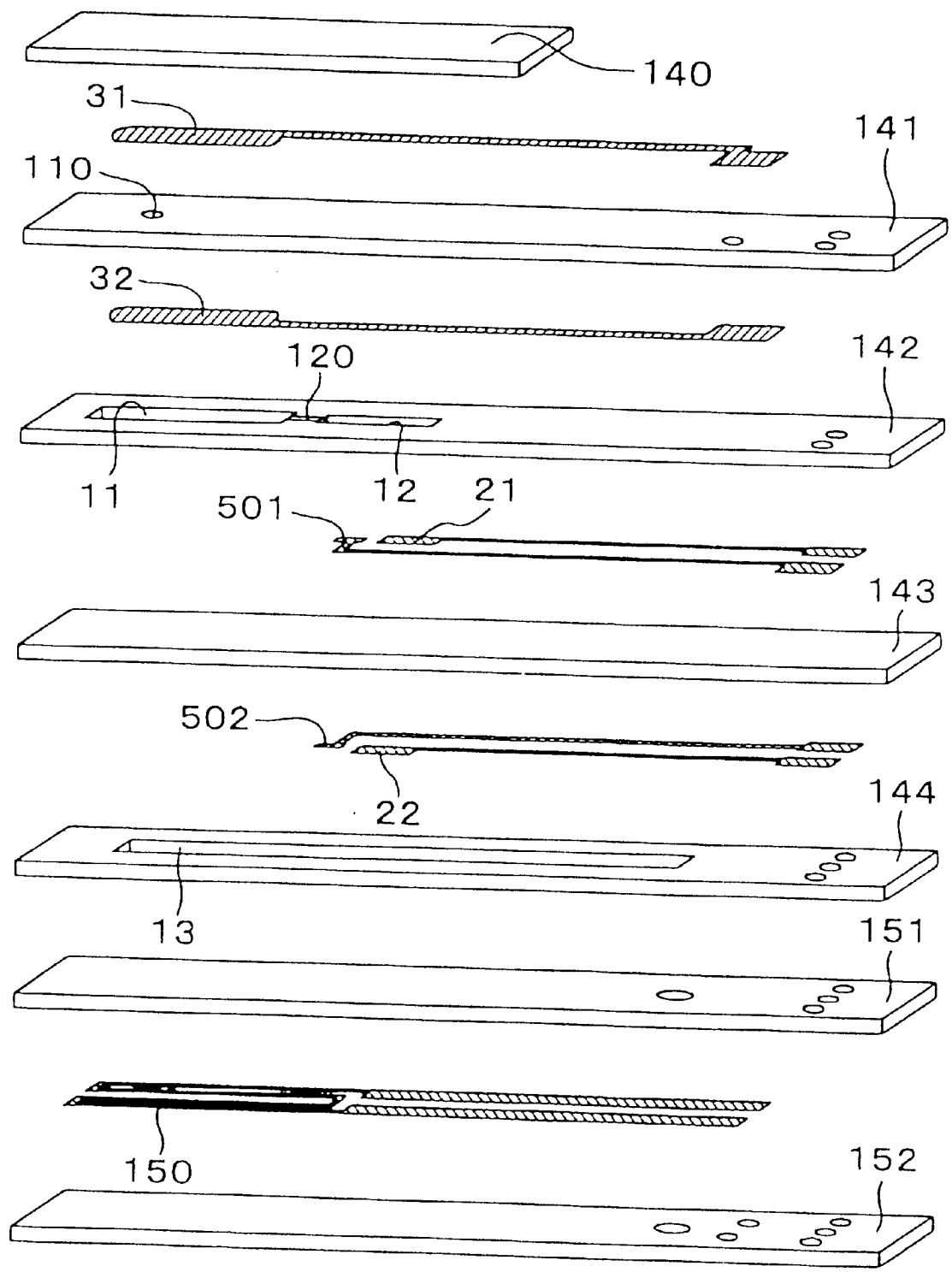
FIG. 14 is a perspective exploded view showing the gas sensing element in accordance with the third embodiment of the present invention.
Figure 15:
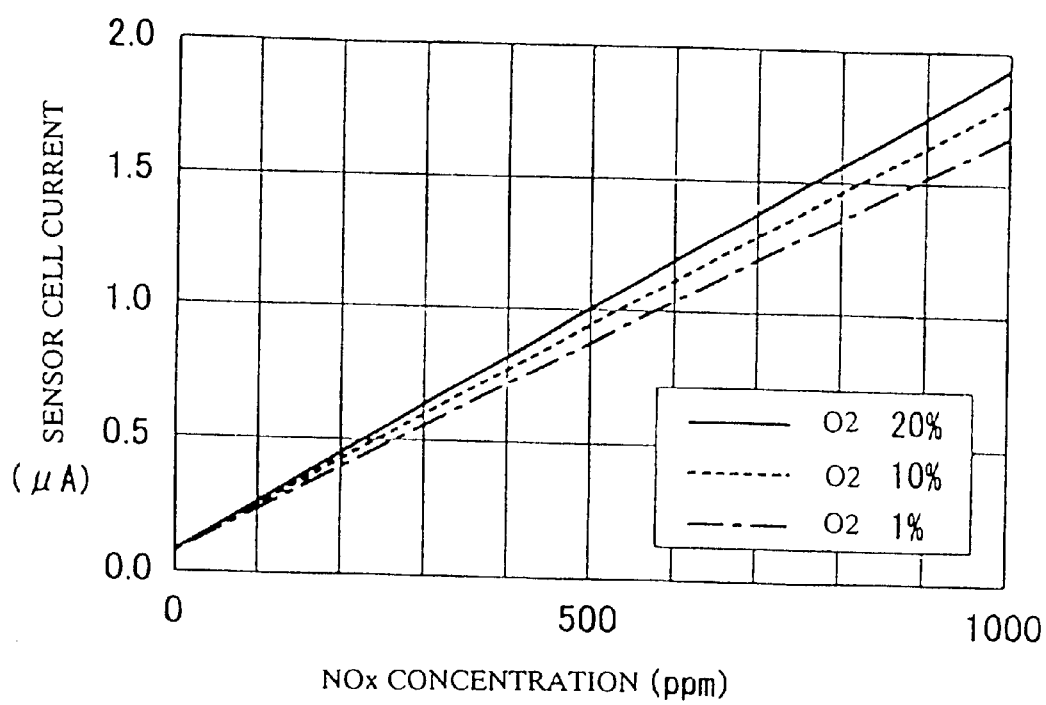
FIG. 15 is a graph showing relationship between NOx concentration and related oxygen ion current in accordance with the third embodiment of the present invention.

As shown in FIGS. 13 to 15, a gas sensing element of a third embodiment has a monitor cell provided in the second chamber 12.

As shown in FIGS. 13 and 14, the gas sensing element 1 of the third embodiment has the pump cell 3 facing the first chamber 11 for pumping oxygen in response to applied voltage. A monitor cell 500 faces the second chamber 12. The sensor cell 2 faces the second chamber 12 for measuring NOx concentration in the measured gas in response to applied voltage.

The voltage applied to pump cell 3 is controlled based on a limiting current obtained when a voltage is applied to the monitor cell 500.

The monitor cell 500 consists of a pair of electrodes 501 and 502 provided on upper and lower surfaces of the second solid electrolytic sheet 143. The monitor cell electrodes 501 and 502 are connected to an ammeter 555 and a power source 556 to constitute a monitor circuit 550.

A feedback circuit 560 is provided to send an output of the ammeter 555 to the pump circuit 35.

The rest of arrangement is identical with that of the first embodiment.

According to this arrangement, monitor cell current does not vary in a specific voltage range irrespective of change of applied voltage to the monitor cell 500. This is referred to as a limiting current. The limiting current represents the oxygen concentration in the second chamber 12. Thus, the limiting current obtained from the monitor cell 500 can be used to control the voltage applied to the pump cell 3.

As the pump cell 3 is controlled based on the oxygen concentration in the vicinity of the sensor cell 2, it becomes possible to accurately detect the NOx concentration even when there is certain distribution in the oxygen gas concentration.

Furthermore, always applying a voltage to the monitor cell 500 makes it possible to perform pumping of oxygen in the second chamber 12.

Accordingly, even in a situation that the pump cell 3 cannot control the oxygen concentration in the first chamber 11 to a constant value due to rapid variation of oxygen concentration in the measured gas, the pumping function of monitor cell 500 can follow up the variation of oxygen concentration. No problem will occur due to the delay in response.

Accordingly, the gas sensing element of the third embodiment makes it possible to accurately detect a specific gas concentration irrespective of stable/unstable state of the oxygen concentration.

Furthermore, as the gas sensing element of the third embodiment uses the limiting current of the monitor cell 500 to control the pump cell 3, it becomes possible to reduce error caused by the offset current. Thus, highly accurate detection is realized.

FIG. 15 shows the result of performance evaluation 1 on the third embodiment performed in the same manner as in the first embodiment.

The result of FIG. 15 demonstrates that the gas sensing element 1 of the third embodiment can accurately detect the NOx concentration even when there is certain distribution in the oxygen gas concentration.

Regarding the performance evaluation 2, the gas sensing element 1 of the third embodiment has obtained substantially the same result as that of the first embodiment (refer to FIG. 6).

Fourth Embodiment

As shown in FIGS. 16 to 21, the gas sensing element 1 of the fourth embodiment comprises first and second pump cells facing the first and second chambers.

Figure 16:
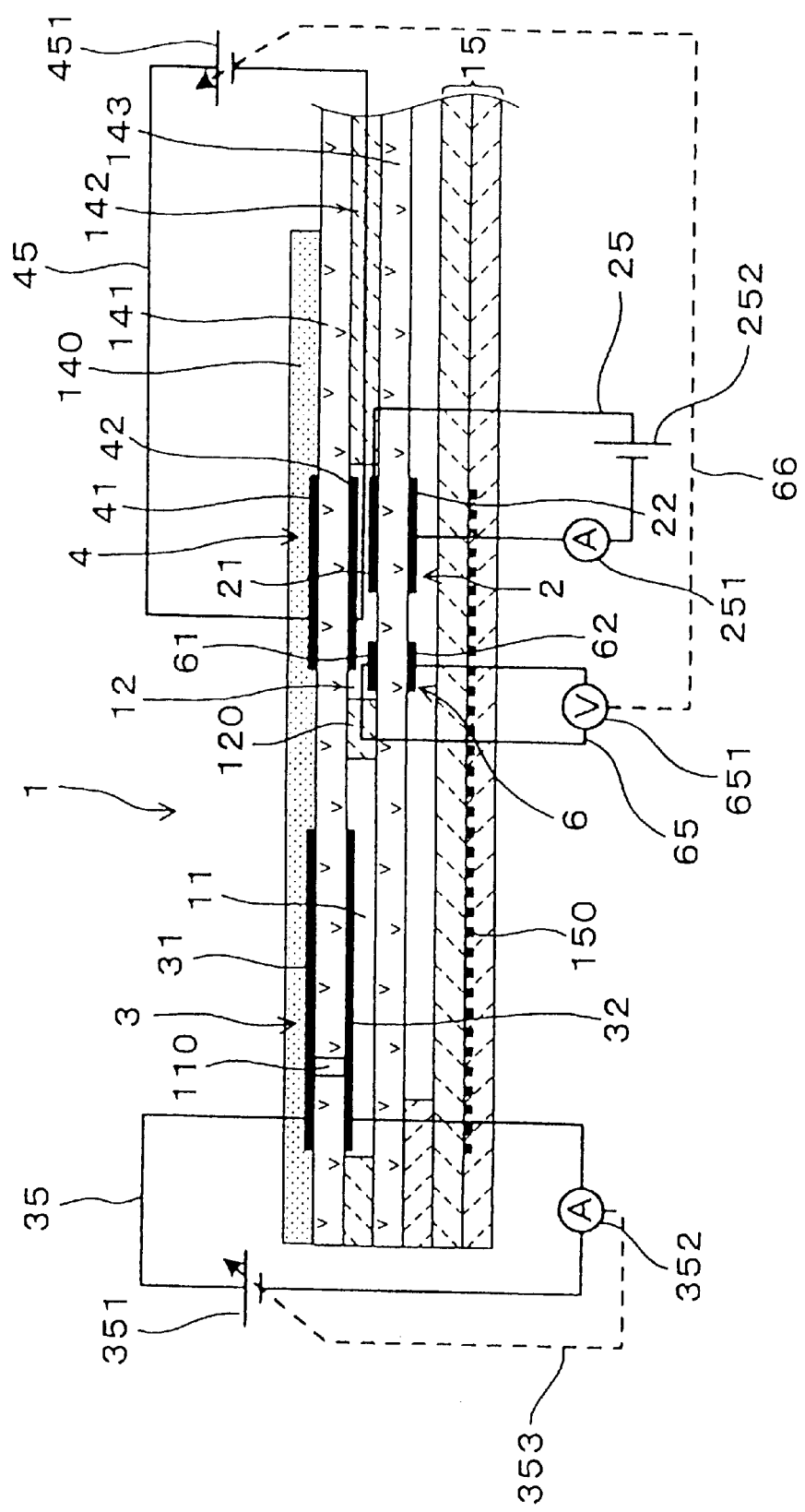
FIG. 16 is a cross-sectional view showing a gas sensing element in accordance with a fourth embodiment of the present invention.
Figure 17:
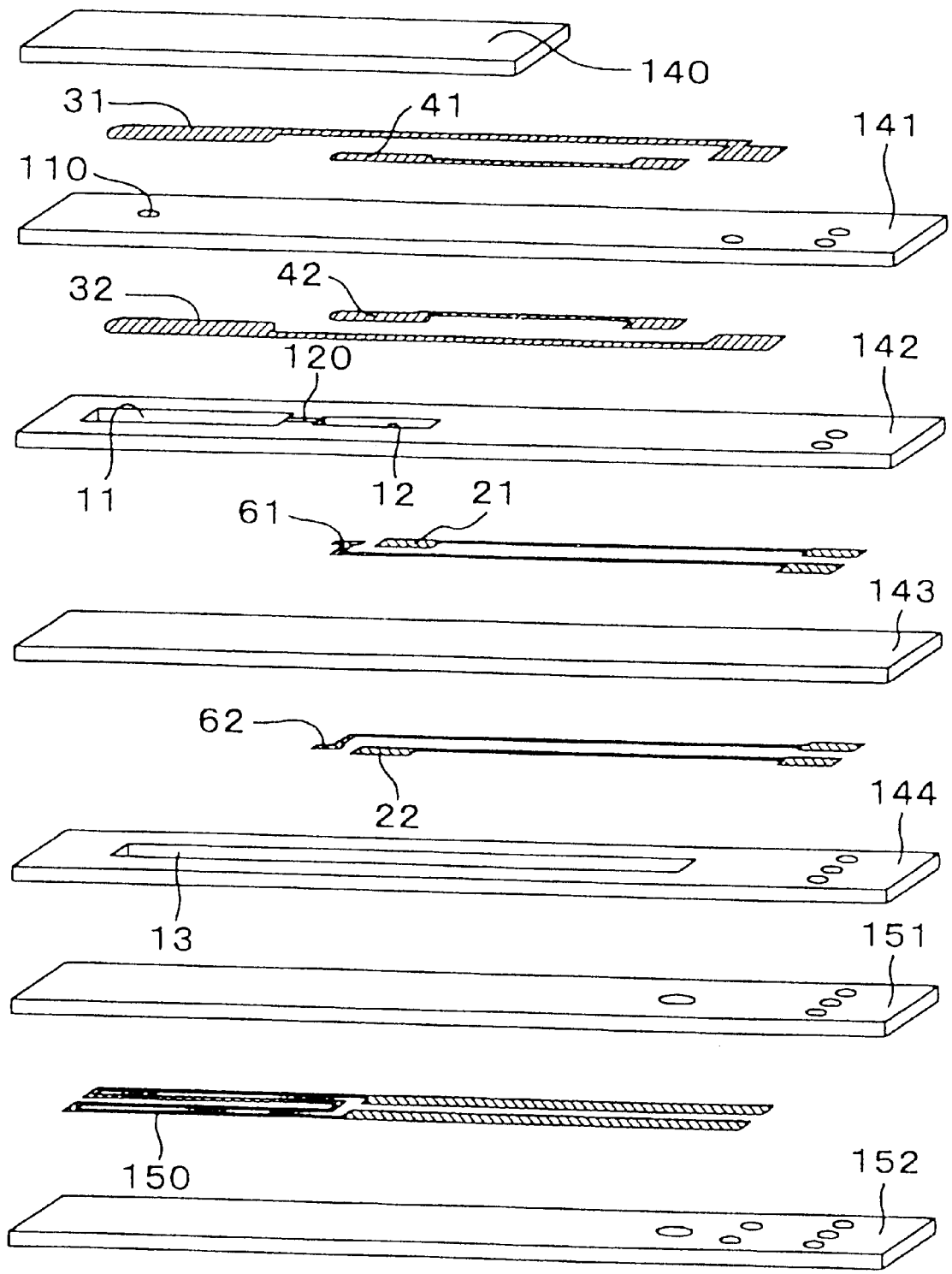
FIG. 17 is a perspective exploded view showing the gas sensing element in accordance with the fourth embodiment of the present invention.

As shown in FIGS. 16 and 17, the gas sensing element 1 has a first pump cell 3 located or provided on a surface defining the first chamber 11 and a second pump cell 4 located or provided on a surface defining the second chamber 12. A sensor cell 2 and a monitor cell 6 are located or provided on a surface defining the second chamber 12.

The first pump cell 3 produces a pump current in accordance with its own oxygen pumping function. The pump current of the first pump cell 3 is utilized to control the voltage applied to first pump cell 3.

The voltage applied to second pump cell 4 is controlled based on an output of a monitor cell 6 facing the second chamber 12.

The first pump cell 3 consists of a pair of electrodes 31 and 32 provided on upper and lower surfaces of the first solid electrolytic sheet 141. The pump cell electrodes 31 and 32 are connected to an ammeter 352 and a power source 351 to constitute a first pump circuit 35.

The second pump cell 4 consists of a pair of electrodes 41 and 42 provided on upper and lower surfaces of the first solid electrolytic sheet 141. The pump cell electrodes 41 and 42 are connected to a power source 451 to constitute a second pump circuit 45.

The monitor cell 6 consists of a pair of electrodes 61 and 62 provided on upper and lower surfaces of the second solid electrolytic sheet 143. The monitor cell electrodes 61 and 62 are connected to a power source 651 to constitute a monitor circuit 65. A feedback circuit 66 is provided to send an output of monitor circuit 65 to the second pump circuit 45.

The rest of arrangement is identical with that of the first embodiment.

Figure 18:
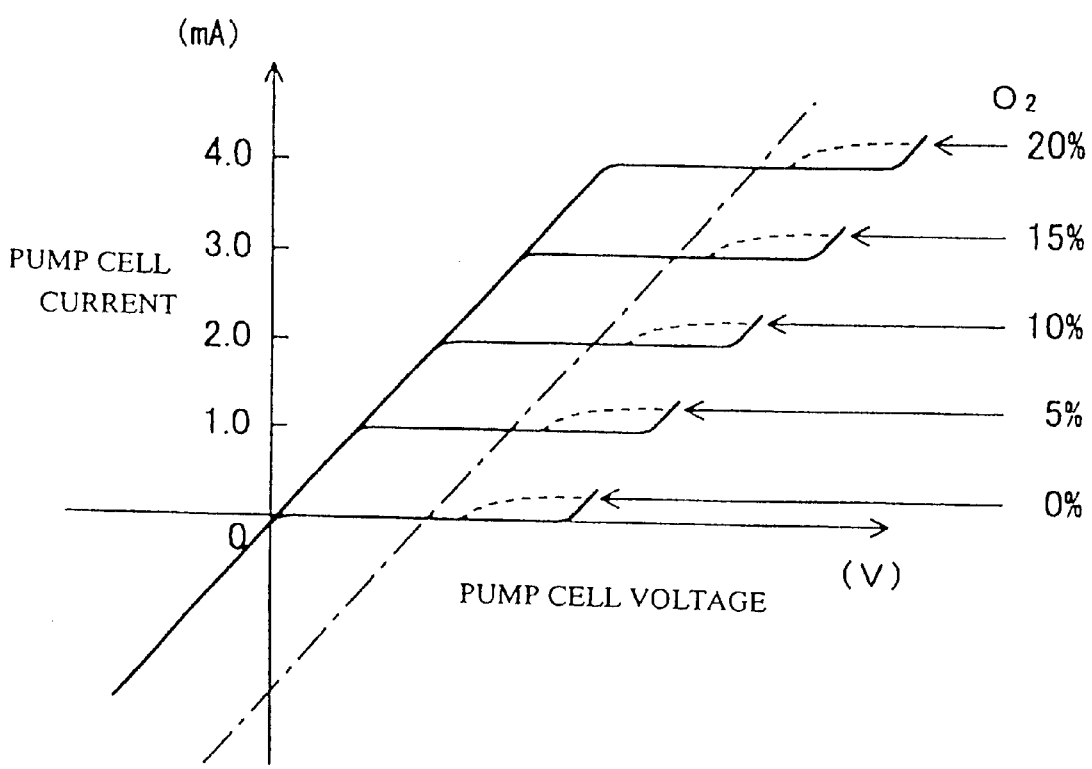
FIG. 18 is a graph showing relationship between pump cell voltage and pump cell current in accordance with the fourth embodiment of the present invention.

As shown in FIG. 18, the pump cell current does not change in a specific voltage range of the applied voltage. This constant current value, i.e., the limiting current value, is dependent on the oxygen concentration.

Accordingly, the oxygen concentration in the first chamber can be maintained at a constant value by adjusting the voltage applied to the pump cell 3 in accordance with the pump current.

Furthermore, according to this embodiment, two pump cells 3 and 4 individually perform pumping in respective chambers 11 and 12. Thus, the oxygen concentration in each of the changers 11 and 12 can be easily controlled to a low value. Even in a situation where the oxygen concentration is widely changing, individually performing the pumping in each chamber makes it possible to eliminate the problem caused due to delay in response.

As described above, the forth embodiment of the present invention provides a gas sensing element which has excellent response and is capable of accurately detecting a specific gas concentration in a measured gas irrespective of unpredictable or unstable distribution of oxygen gas concentration.

According to the performance evaluations 1 and 2, the gas sensing element 1 of the fourth embodiment has obtained substantially the same result as that of the first embodiment (refer to FIGS. 5 and 6). This demonstrates that the gas sensing element of the fourth embodiment has excellent response and is capable of accurately detecting the NOx concentration irrespective of oxygen concentration.

Figure 19:
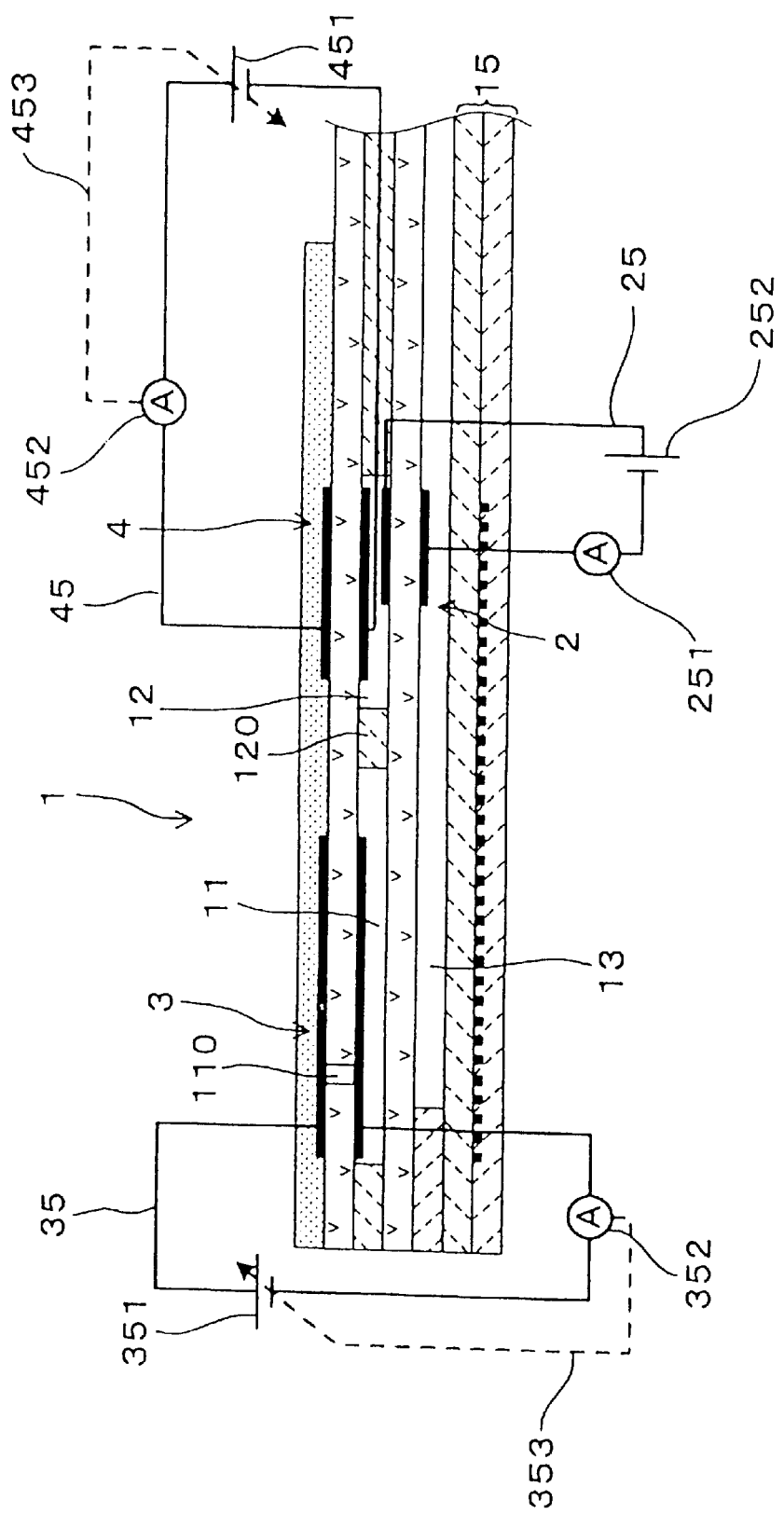
FIG. 19 is a cross-sectional view showing another gas sensing element in accordance with the fourth embodiment of the present invention.

FIG. 19 shows a modified gas sensing element 1 in accordance with the fourth embodiment, according to which the second pump cell 4 produces a pump current in accordance with its own oxygen pumping function. The pump current of the second pump cell 4 is utilized to control the voltage applied to second pump cell 4. The second pump cell 4 is connected to an ammeter 452 and a power source 451 to constitute a pump circuit 45. A feedback circuit 453 is provided to send an output of the ammeter 452 to the power source 451. This modified embodiment brings substantially the same effects as that shown in FIG. 16.

Fifth Embodiment

Figure 20:
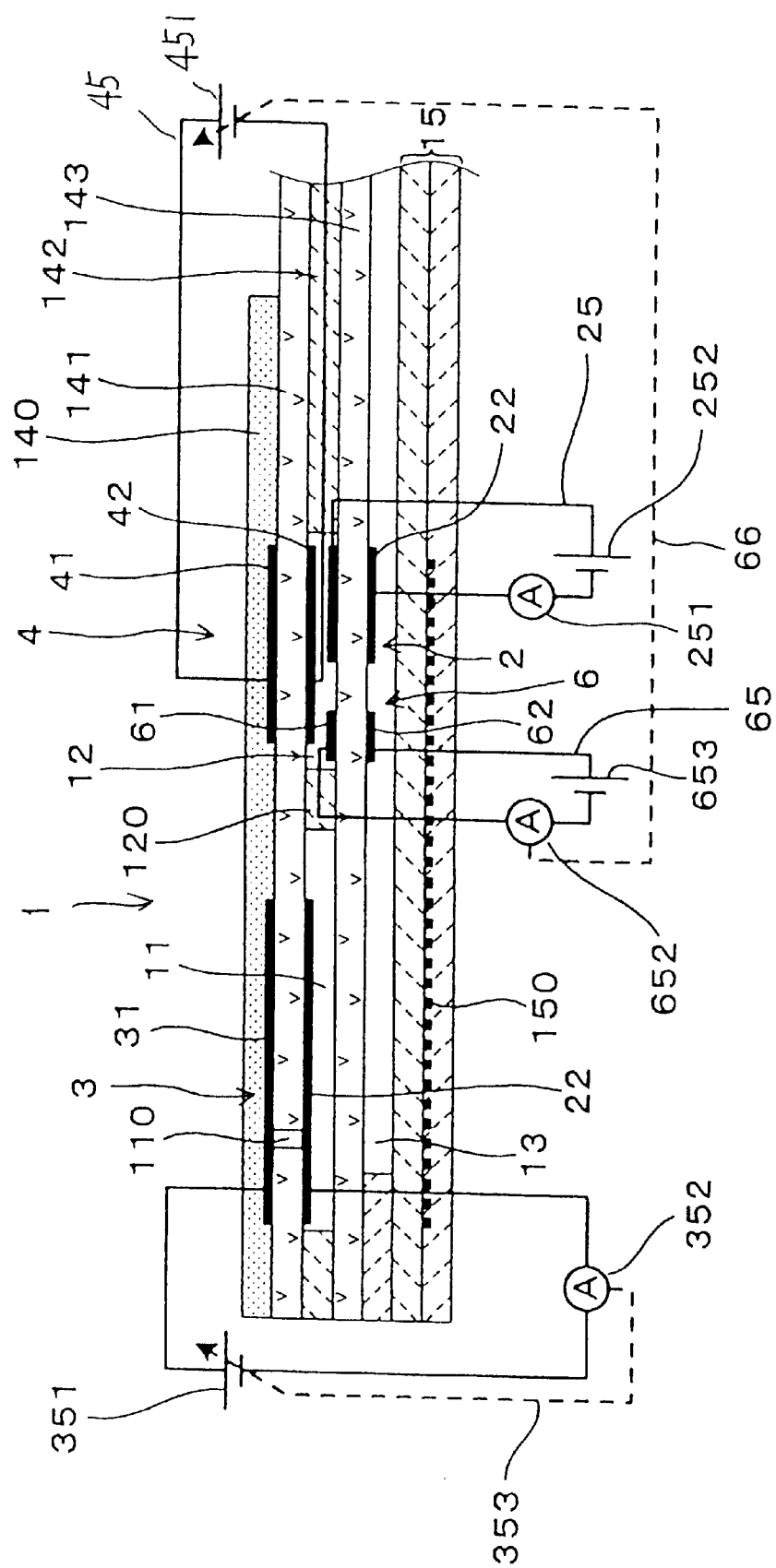
FIG. 20 is a cross-sectional view showing a gas sensing element in accordance with a fifth embodiment of the present invention.

FIG. 20 shows a gas sensing element in accordance with a fifth embodiment of the present invention.

Like the fourth embodiment, the first pump cell 3 produces a pump current in accordance with its own oxygen pumping function. The pump current of the first pump cell 3 is utilized to control the voltage applied to first pump cell 3.

It is however possible to provide a monitor cell between the first chamber and a reference gas chamber. In this case, an output of this monitor cell can be used to control the voltage applied to the first pump cell 3 so that the monitor cell can produce a constant electromotive force. Alternatively, when a voltage is applied to the monitor cell, it is possible to control the monitor cell current to a constant value.

The voltage applied to the second pump cell 4 is controlled in such a manner that the monitor cell 6 produces a constant monitor current. The monitor cell 6 faces the second chamber 12 and is applied a voltage from a power source 653. An ammeter 652 detects the monitor current of the monitor cell 6. The monitor cell 6, ammeter 652, and power source 653 cooperatively constitute a monitor circuit 65. A feedback circuit 66 is provided to send an output of the ammeter 652 to the power source 451 of the pump circuit 45.

According to the gas sensing element 1 of the fifth embodiment, it becomes possible to accurately detect the NOx concentration in the measured gas without being aversely influenced by the offset of sensor cell current, while maintaining proper response.

According to the performance evaluations 1 and 2, the gas sensing element 1 of the fifth embodiment has obtained substantially the same result as that of the first embodiment (refer to FIGS. 5 and 6). This demonstrates that the gas sensing element of the fourth embodiment has excellent response and is capable of accurately detecting the NOx concentration irrespective of oxygen concentration.

Sixth Embodiment

Figure 21:
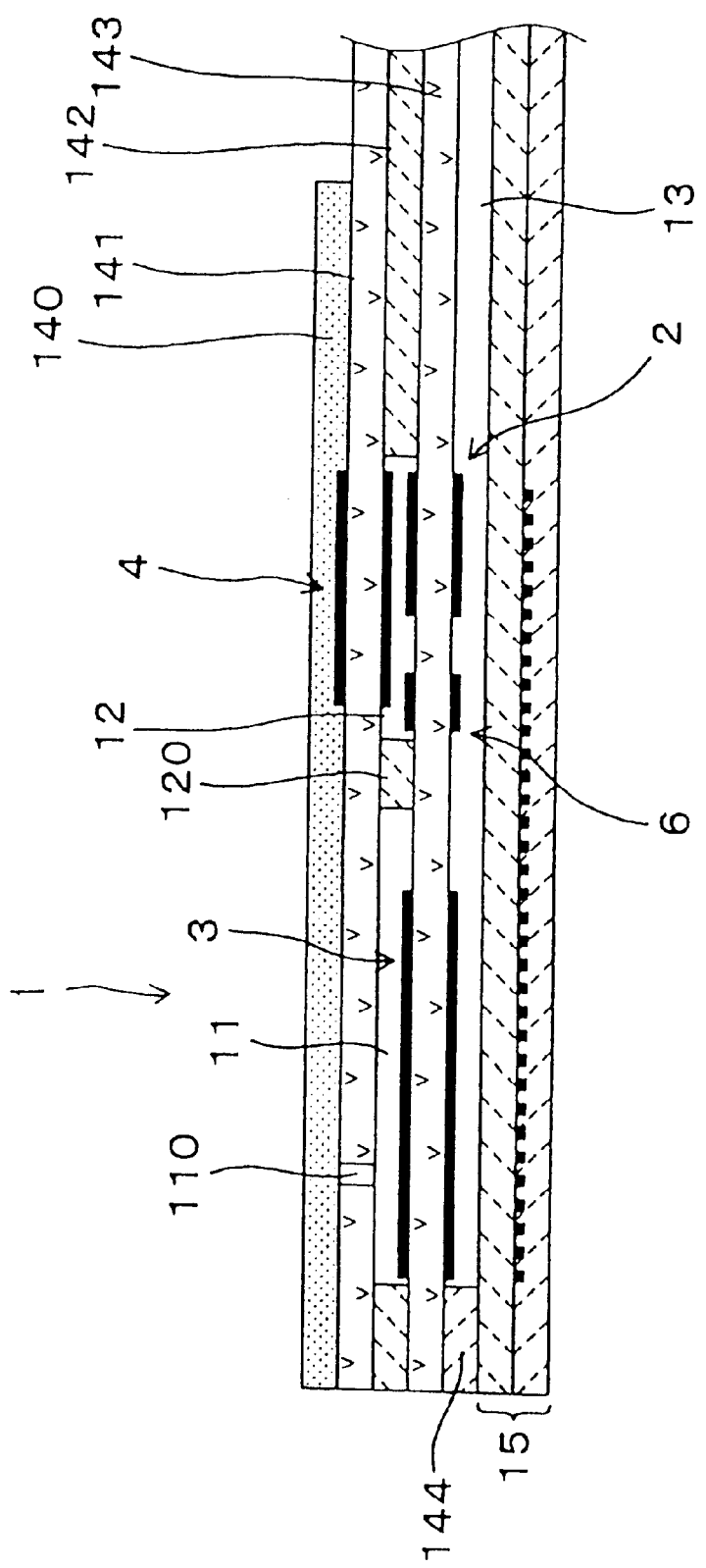
FIG. 21 is a cross-sectional view showing a gas sensing element in accordance with a sixth embodiment of the present invention.

FIG. 21 shows a gas sensing element in accordance with a sixth embodiment of the present invention. The pump cell 3 is provided between the first chamber 11 and the reference gas chamber 13 so as to perform pumping of oxygen between them. The reference gas chamber 13 is filled with air. When used for measurement of exhaust gas emitted from an automotive engine, the gas sensing element of the sixth embodiment can accurately measure the NOx concentration even when the air-fuel ratio of the exhaust gas is shifted to a lean side. The rest of the sixth embodiment is substantially the same as that of the fourth embodiment.

Seventh Embodiment

Figure 22:
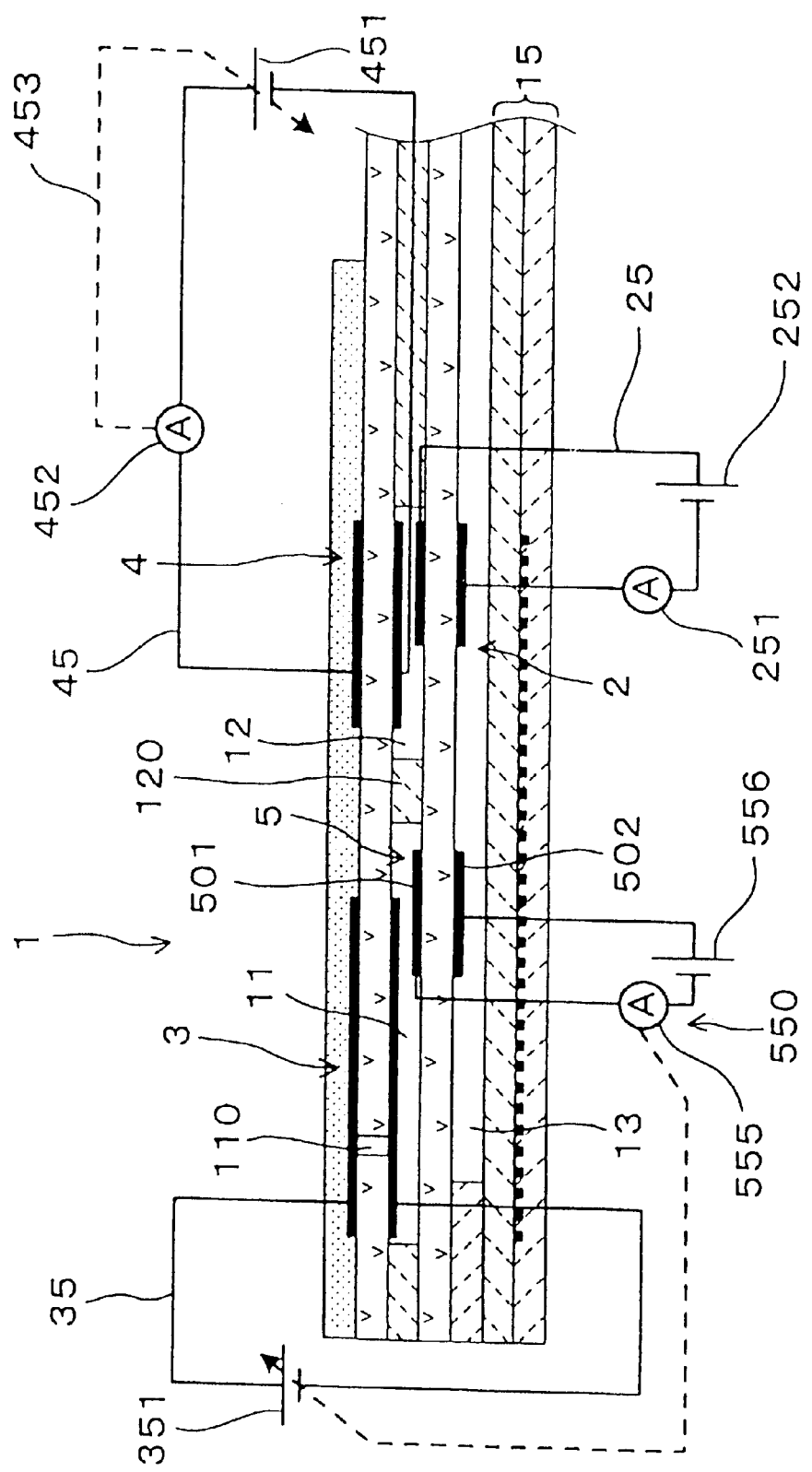
FIG. 22 is a cross-sectional view showing a gas sensing element in accordance with a seventh embodiment of the present invention.

FIG. 22 shows a gas sensing element in accordance with a seventh embodiment of the present invention, according to which both the first pump cell 3 and the monitor cell 5 face the first chamber 11 while both the second pump cell 4 and the sensor cell 2 face the second chamber 12. The voltage applied to the first pump cell 3 is controlled based on a limiting current of the monitor cell 5. The voltage applied to the second pump cell 4 is controlled based on its own pump current.

However, as the oxygen concentration in the second chamber is a lower constant value, it is possible to apply a constant voltage to set the second pump cell 4.

Furthermore, it is possible to provide a monitor cell between the second chamber and the reference gas chamber, so that an electromotive force generated from the monitor cell can be used to control the voltage applied to the second pump cell.

Figure 23:
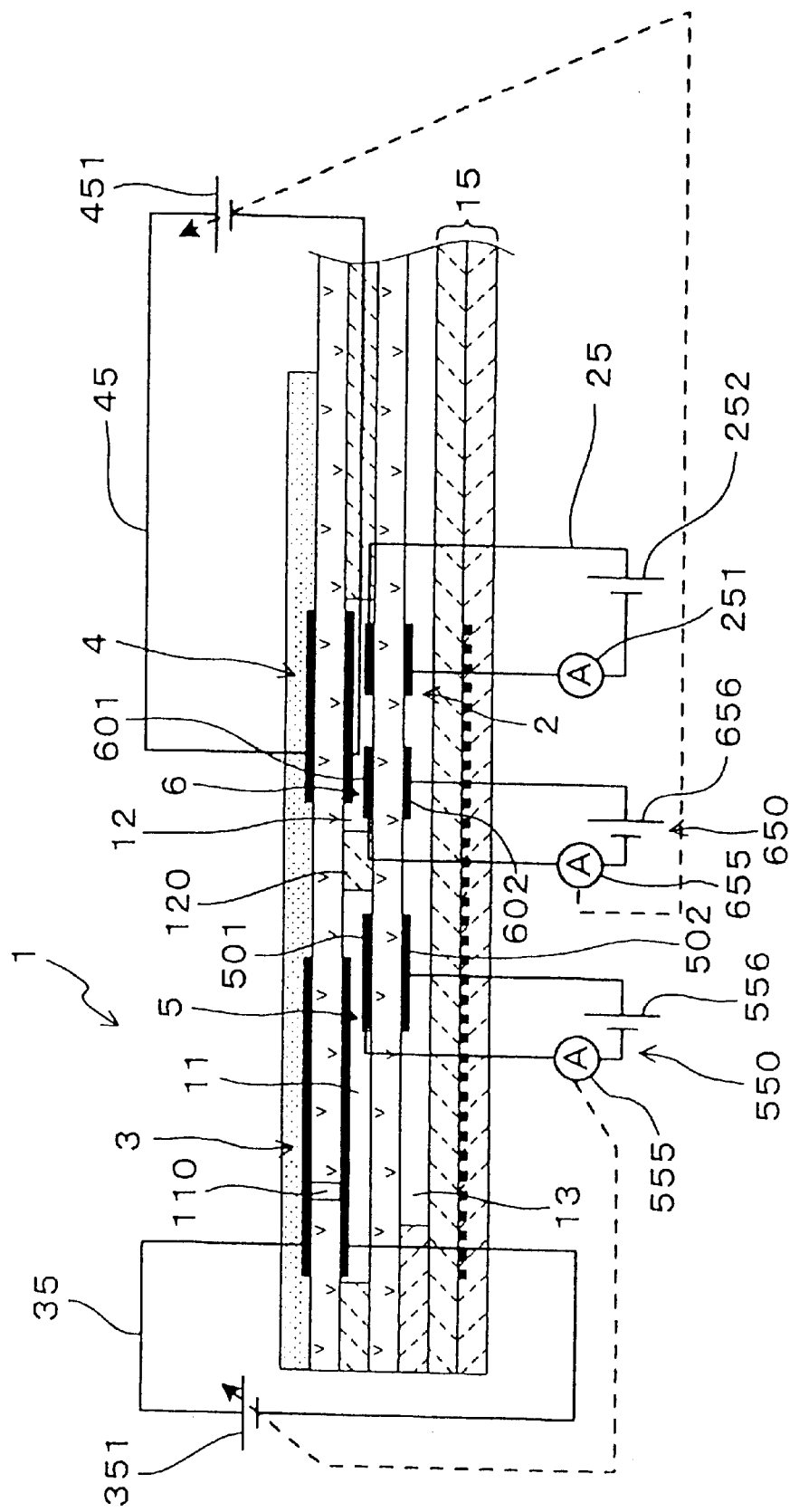
FIG. 23 is a cross-sectional view showing another gas sensing element in accordance with the seventh embodiment of the present invention.

FIG. 23 shows another gas sensing element in accordance with the seventh embodiment of the present invention. Both the first pump cell 3 and the first monitor cell 5 face the first chamber 11. The second pump cell 4, the second monitor cell 6, and the sensor cell 2 face the second chamber 12. The first monitor cell 5 is connected to an ammeter 555 and a power source 556 to constitute a first monitor circuit 550. The second monitor cell 6 is connected to an ammeter 655 and a power source 656 to constitute a second monitor circuit 650.

The voltage applied to the first pump cell 3 is controlled based on a limiting current of the first monitor cell 5. The voltage applied to the second pump cell 4 is controlled based on a limiting current of the second monitor cell 6.

According to the gas sensing element 1 of the seventh embodiment, it becomes possible to accurately detect the NOx concentration in the measured gas without being aversely influenced by the offset of sensor cell current, while maintaining proper response.

Eighth Embodiment

Figure 24:
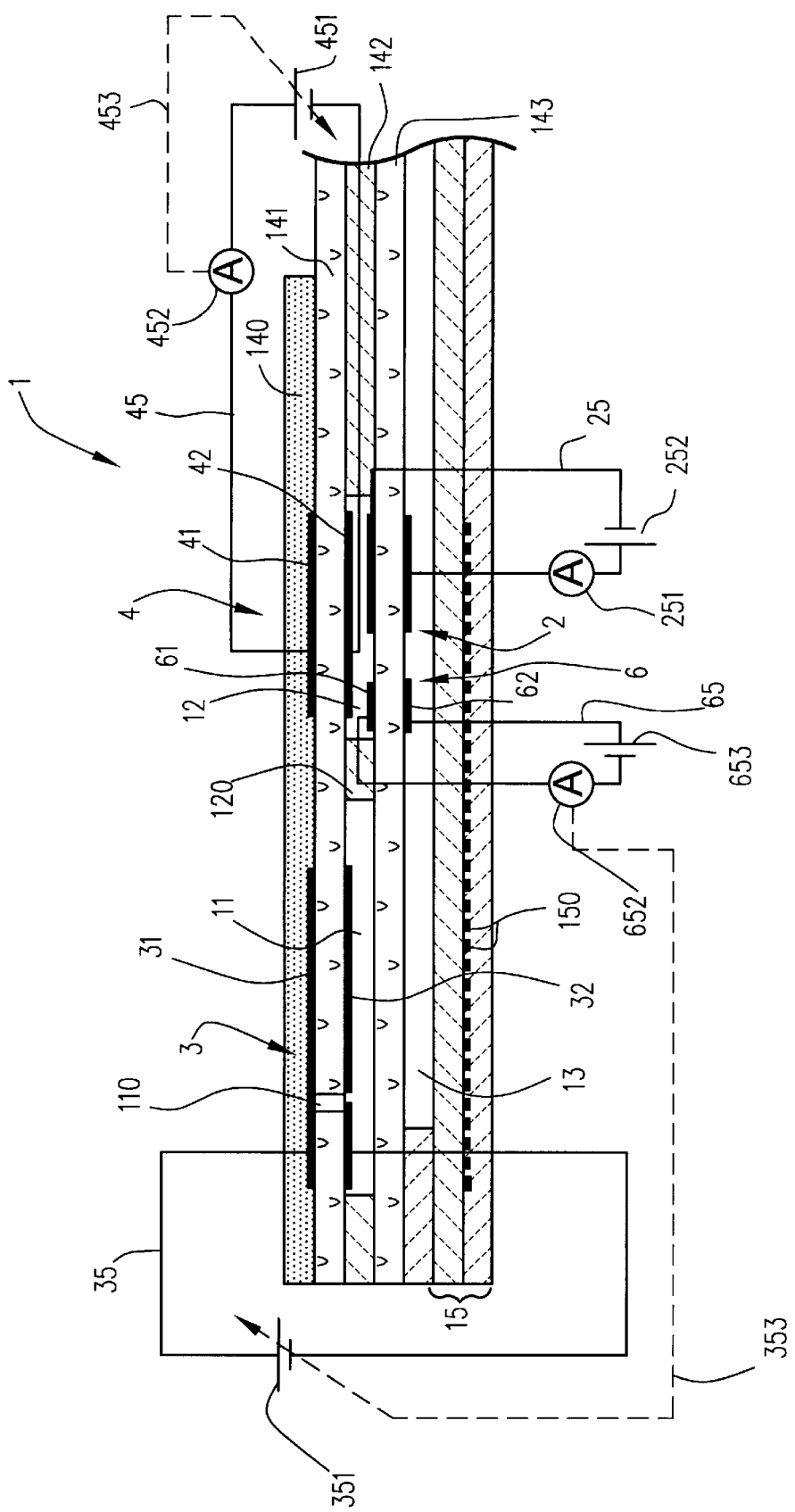
FIG. 24 is a cross-sectional view showing a gas sensing element in accordance with an eighth embodiment of the present invention.

FIG. 24 shows a gas sensing element in accordance with an eighth embodiment of the present invention, according to which the first pump cell 3 faces the first chamber 11 while both the second pump cell 4 and the monitor cell 6 face the second chamber 12. The voltage applied to the first pump cell 3 is controlled based on a limiting current of the monitor cell 6. The voltage applied to the second pump cell 4 is controlled based on its own pump current.

It is however possible to provide a monitor cell between the second chamber and the reference gas chamber. In this case, an output of this monitor cell can be used to control the voltage applied to the second pump cell 4 so that the monitor cell can produce a constant electromotive force.

Figure 25:
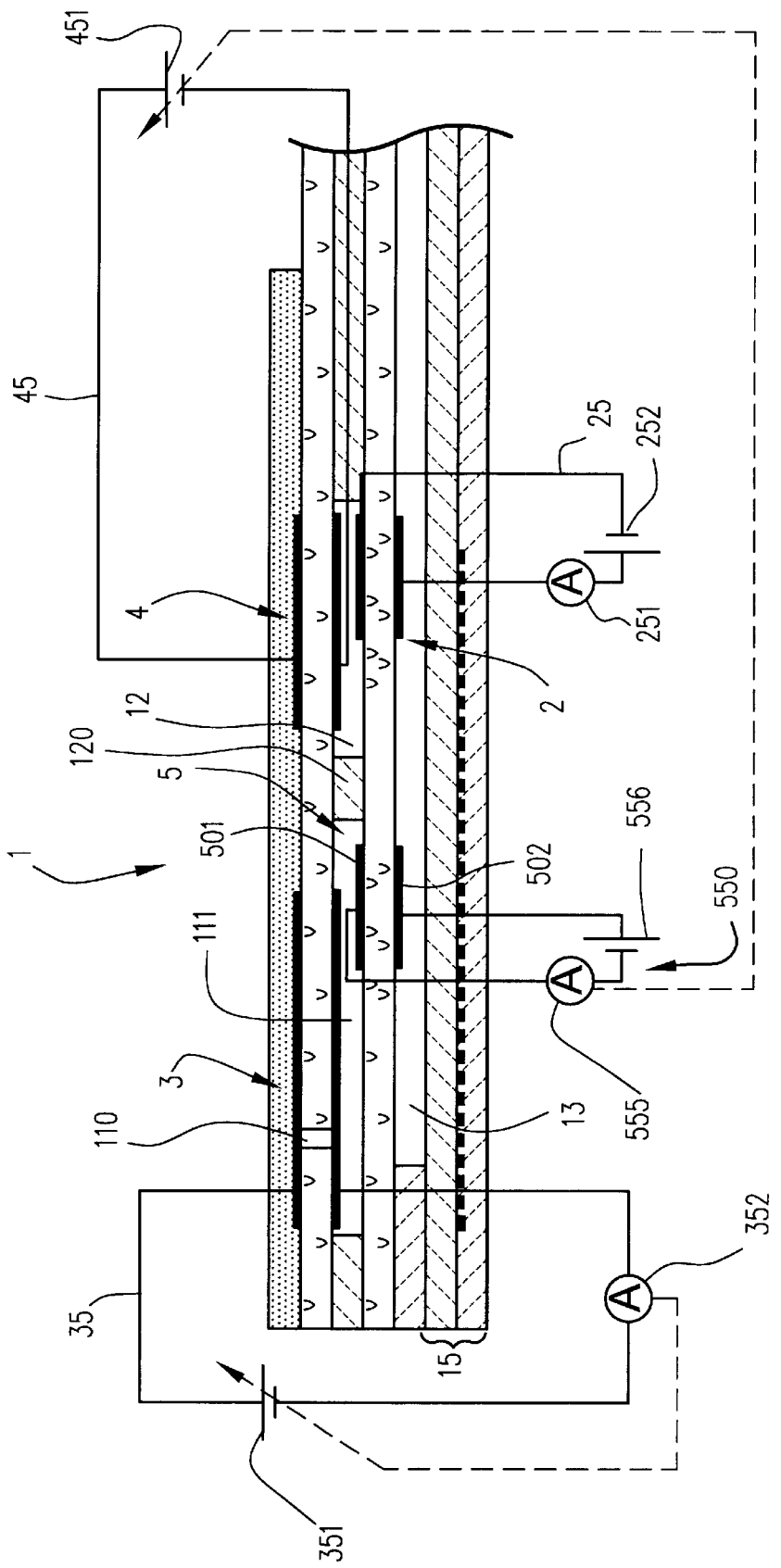
FIG. 25 is a cross-sectional view showing another gas sensing element in accordance with the eighth embodiment of the present invention.

FIG. 25 shows another gas sensing element in accordance with the eighth embodiment of the present invention, according to which both the first pump cell 3 and monitor cell 5 face the first chamber 11 while both the second pump cell 4 and the sensor cell 2 face the second chamber 12. The voltage applied to the first pump cell 3 is controlled based on its own pump current. The voltage applied to the second pump cell 4 is controlled based on a limiting current of the monitor cell 5.

It is however possible to provide a monitor cell between the first chamber and the reference gas chamber. In this case, an output of this monitor cell can be used to control the voltage applied to the first pump cell 3 so that the monitor cell can produce a constant electromotive force.

According to the gas sensing element 1 of the eighth embodiment, it becomes possible to accurately detect the NOx concentration in the measured gas without being aversely influenced by the offset of sensor cell current, while maintaining proper response.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A gas sensing element comprising:

first and second chambers into which an objective gas to be measured is introduced;

a first diffusion resistive passage connecting said first chamber to an outside of said gas sensing element;

a second diffusion resistive passage connecting said first chamber to said second chamber;

a pump cell provided on a surface defining said first chamber for pumping oxygen in accordance with an applied voltage;

a first monitor cell provided on a surface defining said first chamber for generating an electromotive force representing an oxygen concentration in said first chamber;

a second monitor cell provided on a surface defining said second chamber for generating an electromotive force representing an oxygen concentration in said second chamber; and a sensor cell provided on a surface defining said second chamber and responsive to application of a predetermined voltage for generating a sensor current representing a specific gas concentration in said objective gas, wherein said voltage applied to said pump cell is controlled based on a difference between the electromotive forces obtained from said first and second monitor cells.

2. The gas sensing element in accordance with claim 1, wherein said first monitor cell and said second monitor cell are connected in parallel with each other.

3. A gas sensing element comprising:

first and second chambers into which an objective gas to be measured is introduced;

a first diffusion resistive passage connecting said first chamber to an outside of said gas sensing element;

a second diffusion resistive passage connecting said first chamber to said second chamber;

a first pump cell provided on a surface defining said first chamber for pumping oxygen in accordance with an applied voltage;

a second pump cell provided on a surface defining said second chamber for pumping oxygen in accordance with an applied voltage;

a sensor cell provided on a surface defining said second chamber and responsive to application of a predetermined voltage for generating a sensor current representing a specific gas concentration in said objective gas, wherein a pump current is produced from at least one of said first and second pump cells in accordance with the pumping of oxygen, and said pump current is utilized to control the voltage applied to said one of said first and second pump cells.

4. The gas sensing element in accordance with claim 3, wherein a monitor cell is provided on a surface defining said first chamber or a surface defining said second chamber, and said voltage applied to at least one of said first and second pump cells is controlled based on a limiting current obtained when a voltage is applied to said monitor cell.

5. The gas sensing element in accordance with claim 4, wherein said first pump cell is provided on a surface defining a reference gas chamber.

6. The gas sensing element in accordance with claim 3, wherein said first pump cell is provided on a surface defining a reference gas chamber.

* * * * *